US009642355B2

(12) United States Patent
Czerwinski

(10) Patent No.: US 9,642,355 B2
(45) Date of Patent: May 9, 2017

(54) CRYOPRESERVATION OF CELLS AND SUBCELLULAR FRACTIONS

(71) Applicant: XenoTech, LLC, Lenexa, KS (US)

(72) Inventor: Maciej Czerwinski, Fairway, KS (US)

(73) Assignee: XENOTECH, LLC, Kansas City, KS (US)

( * ) Notice: Subject to any disclaimer, the term of this patent is extended or adjusted under 35 U.S.C. 154(b) by 0 days.

(21) Appl. No.: 14/856,199

(22) Filed: Sep. 16, 2015

(65) Prior Publication Data
US 2016/0000065 A1 Jan. 7, 2016

Related U.S. Application Data

(62) Division of application No. 12/871,393, filed on Aug. 30, 2010.

(60) Provisional application No. 61/340,259, filed on Mar. 15, 2010, provisional application No. 61/256,833, filed on Oct. 30, 2009.

(51) Int. Cl.
A01N 1/02 (2006.01)
C12N 5/071 (2010.01)

(52) U.S. Cl.
CPC ............ A01N 1/0284 (2013.01); A01N 1/02 (2013.01); A01N 1/0268 (2013.01); C12N 5/067 (2013.01)

(58) Field of Classification Search
CPC ...... A01N 1/0284; A01N 1/0268; A01N 1/02; C12N 5/067
See application file for complete search history.

(56) References Cited

U.S. PATENT DOCUMENTS

| 7,604,929 | B2 | 10/2009 | Dryden et al. |
| 2005/0239042 | A1 | 10/2005 | Dryden et al. |
| 2008/0280357 | A1 | 11/2008 | Arseniev et al. |
| 2009/0130756 | A1 | 5/2009 | Klann et al. |

FOREIGN PATENT DOCUMENTS

| WO | 2007120829 | 10/2007 |
| WO | 2007/147004 | 12/2007 |

OTHER PUBLICATIONS

Hengstler et al., "Cryopreserved Primary Hepatocytes as a Constantly Available in Vitro Model for the Evaluation of Human and Animal Drug Metabolism and Enzyme Induction*," Drug Metabolism Reviews, 2000, 32(1), 81-118.
Alexandre et al., "Cryopreservation of adult human hepatocytes obtained from resected liver biopsies," Cryobiology, 2002, 44, 103-113.
Day, "Cryopreservation: fundamentals, mechanisms of damage on freezing/thawing and application in culture collections," Nova Hedwigia, 2004, 79, 191-205.
Meryman, "Cryopreservation of living cells: principles and practice," Transfusion, 2007, vol. 47, 935-945.
Stephenne, "Cryopreservation of Human Hepatocytes Alters the Mitochondrial Respiratory Chain Complex 1," Cell Transplantation, 2007, vol. 16, 409-419.
Lloyd et al., "Cryopreservation of hepatocytes: a review of current methods for banking," Cell and Tissue Banking, 2003, 4, 3-15.
Dou et al., "Thawed Human Hepatocytes in Primary Culture," Cryobiology, 1992, 29, 454-469.
Adams et al., "Effective Cryopreservation and Long-Term Storage of Primary Human Hepatocytes With Recovery of Viability, Differentiation, and Replicative Potential," Cell Transplantation, 1995, vol. 4, No. 6, pp. 579-586.
Morsiani et al., "Automated Liver Cell Processing Facilitates Large Scale Isolation and Purification of Porcine Hepatocytes," ASAIO Journal, 1995, 41, 155-161.
Seglen, "Preparation of Isolated Rat Liver Cells," Meth. Cell Biol., 1976, 13:29-83.
Li et al., "Isolation and Culturing of Hepatocytes From Human Livers," J. Tiss. Cult. Meth., 1992, 14:139-146.
Yamazaki et al, "Effects of Freezing, Thawing, and Storage of Human Liver Samples on the Microsomal Contents and Activities of Cytochrome P450 Enzymes" Drug Metabolism and Disposition, vol. 25, No. 2, 1997 pp. 168-174.
Hewitt et al., "Cryopreserved rat, dog and monkey hepatocytes: measurement of drug metabolizing enzymes in suspensions and cultures," Human & Experimental Toxicology, 2004, 23: 307-316.
Chesne et al., "Cryopreservation of Isolated Rat Hepatocytes: A Critical Evaluation of Freezing and Thawing Conditions," Cryobiology, 1988, 25, 323-330.
Loretz et al., "Optimization of cryopreservation procedures for rat and human hepatocytes," Xenobiotica, 1989, vol. 19, No. 5, 489-498.
Swales et al., "Cryopreservation of Rat and Mouse Hepatocytes. II. Assessment of Metabolic Capacity Using Testosterone Metabolism," Drug Metabolism and Disposition, 1996, vol. 24, No. 11, 1224-1230.
Swales et al., "Cryopreservation of Rat and Mouse Hepatocytes. I. Comparative Viability Studies," Drug Metabolism and Disposition, 1996, vol. 24, No. 11, 1218-1223.
Parkinson et al., "Preparation of Hepatocytes," Current Protocols in Toxicology, 2001, 14.2.1-14.2.13, John Wiley & Sons, Inc.
Madan et al., "Effect of Cryopreservation on Cytochrome P-450 Enzyme Induction in Cultured Rat Hepatocytes," Drug Metabolism and Disposition, 1999, vol. 27, No. 3, 327-335.
Quistorff et al., "Preparation of Isolated Rat Liver Hepatocytes," Methods in Molecular Biology, 1990, vol. 5, Chapter 14, 151-160.

(Continued)

Primary Examiner — Taeyoon Kim
(74) Attorney, Agent, or Firm — Hovey Williams LLP

(57) ABSTRACT

The invention provides cryopreserved compositions of cells, wherein the compositions are advantageously in the form of self-sustaining bodies that can be individually handled and combined independently of a container, allowing for easy customization of the eventual pooled preparation. The invention also provides pre-pooled stacks of the self-sustaining cryopreserved compositions for eventual thawing to produce pooled preparations of cells. A mold and methods for forming the self-sustaining bodies are also provided. The invention is also concerned with methods of forming pooled preparations of cells using single-cryopreserved compositions of cells.

18 Claims, 9 Drawing Sheets

(56) References Cited

OTHER PUBLICATIONS

Pikal-Cleland et al., "Protein Denaturation during Freezing and Thawing in Phosphate Buffer Systems: Monomeric and Tetrameric B-Galactosidase," Archives of Biochemistry and Biophysics, 2000, vol. 384, No. 2, 398-406.
Harris et al., "Cryopreservation of Isolated Hepatocytes: Intracellular Ice Formation under Various Chemical and Physical Conditions," Cryobiology, 1991, 28, 436-444.
Chesne et al., "Viability and Function in Primary Culture of Adult Hepatocytes from Various Animal Species and Human Beings After Cryopreservation," Hepatology, 1993, vol. 18, No. 2, 406-414.
Shaddock et al., "Cryopreservation and Long-Term Storage of Primary Rat Hepatocytes: Effects on Substrate-Specific Cytochrome P450-Dependent Activities and Unscheduled DNA Synthesis," Cell Biology and Toxicology, 1993, vol. 9, No. 4, 345-357.
Corsini et al., "Serum-Free Cryopreservation of Five Mammalian Cell Lines in Either a Prelleted or Suspended State," Biol Proced Online, vol. 6, No. 1, 2004, pp. 61-66.
International Search Report and Written Opinion dated May 30, 2011, in related PCT/US2010/047153 filed Aug. 30, 2010.

CRYOPRESERVATION OF CELLS AND SUBCELLULAR FRACTIONS

CROSS-REFERENCE TO RELATED APPLICATIONS

The present application is a divisional of U.S. patent application Ser. No. 12/871,393, filed Aug. 30, 2010, which claims the benefit of and priority from U.S. Provisional Patent Application Ser. No. 61/340,259, filed Mar. 15, 2010, and U.S. Provisional Patent Application Ser. No. 61/256,833, filed Oct. 30, 2009, the entire disclosures of which are hereby incorporated by reference herein.

BACKGROUND OF THE INVENTION

Field of the Invention

The present invention is broadly concerned with cryopreserved self-sustaining bodies formed from compositions of cells, methods of forming the same, and methods of using the same to produced pooled preparations of cells.

Description of Related Art

Hepatocytes are parenchymal liver cells, and make up 60-80% of the cytoplasmic mass of the liver. Hepatocytes play a key role in the detoxification, modification, and excretion of exogenous and endogenous substances. One of the detoxifying functions of hepatocytes is to modify ammonia to urea for excretion. They are also important in protein synthesis and storage, in the transformation of carbohydrates, and in the synthesis of cholesterol, bile salts, and phospholipids.

Viable intact hepatocytes, isolated from human or laboratory animal livers, offer an experimental model for phase I and phase II drug metabolism studies, as well as enzyme induction studies. Isolated and cultured hepatocytes are also an appropriate model for studying overall liver function. Fresh hepatocytes are obtainable only from liver resections or non-transplantable livers of organ donors. Thus, the availability of viable, fresh liver tissue from humans is inconsistent and overall fairly limited, thus limiting the ability to conduct experiments using such a system, because availability does not always coincide with when such cells are needed. When tissue does become available, the isolated hepatocytes must be cryopreserved and banked for later use. However, individual hepatocyte samples have limited applicability due to individual variation in cell function. For example, due to individual variability in Cytochrome P450 (CYP) expression, studying enzyme induction using hepatocytes isolated from a single donor is usually not representative of a given population's response to a particular new chemical entity (NCE) or drug. Thus, hepatocyte preparations pooled from multiple donors are desirable for studying NCE's, as such pooled preparations provide a composite or "average" hepatocyte preparation. It is therefore desirable to accumulate a bank of cryopreserved hepatocytes from various donors for pooling. In a traditional method of pooling hepatocytes, selected frozen vials from the individual donor bank are thawed, pooled together, and then refrozen. Depending upon the desired pool, all or only a portion of the thawed aliquot is used in the pool. This frozen pooled product is then used for NCE studies.

Cryopreservation is a process where cells or whole tissues are preserved by cooling to low sub-zero temperatures (at least about −90° C.). At these low temperatures, any biological activity, including the biochemical reactions that would lead to cell death, is effectively stopped. Several methods have been used to successfully cryopreserve hepatocytes obtained from laboratory animals and humans. Methods of cryopreservation vary, but cryopreservation of hepatocytes in a medium containing 20-90% fetal bovine serum (FBS) and 10-20% dimethyl sulfoxide (DMSO) as a cryoprotectant yield a high viable cell recovery upon thawing. Density of the hepatocytes in the freezing media may vary from $10^6$ to $10^7$ cells/mL. While the development of cryopreservation methods for the storage of hepatocytes has significantly facilitated the availability of human hepatocytes, cryopreservation has been found to cause significant decrease in cellular viability after thawing. Controlled slow rate freezing minimizes the formation of intracellular ice-crystals, which play a large role in hepatocyte damage during the cryopreservation procedure. Rapid thawing of frozen hepatocytes at 37° C. has also been shown to improve viable cell recoveries. However, the poor recovery of cells following cryopreservation and thawing continues to limit the use of hepatocytes for in vitro liver models. This problem is particularly apparent in traditional pooled hepatocyte preparations, which are prepared using multiple freeze-thaw cycles, where each successive freeze-thaw cycle causes increased damage to at least a portion of the hepatocytes in the preparation, reducing overall cell viability of the resulting pool. Similar problems are encountered during cryopreservation and storage of other cellular and subcellular fractions, such as organelles.

Accordingly, the need remains for processes that would enable the availability of hepatocytes and other organelles for medical research, clinical testing, induction studies, and other purposes. A need further exists for pooled hepatocytes and cellular and subcellular fraction having stable and reproducible characteristics and acceptable viability. In addition, there is a need for pooled products that avoid cryoinjury caused by multiple freeze-thaw cycles on the properties and characteristics of the cells.

SUMMARY OF THE INVENTION

The present invention is broadly concerned with a cryopreserved composition of cells. Advantageously, the composition is in the form of a self-sustaining body that can be handled independently of a container, so that a plurality of the compositions can be assembled for eventual pooling of the compositions into a pooled preparation of cells.

The invention is also directed towards the combination of a first cryopreserved composition of cells and a second cryopreserved composition of cells. The first composition is in the form of a first self-sustaining body, and the second composition is in the form of a second self-sustaining body adjacent to the first self-sustaining body. Advantageously, the first self-sustaining body and second self-sustaining body are in physical contact with each other, but remain discrete bodies.

The invention also provides a method of preparing a first cryopreserved self-sustaining body formed from a composition of cells. The method comprises providing a first receptacle or mold comprising a plurality of wells configured to contain the cells. A quantity of a first composition of cells from a first source is added to each of the wells in the receptacle. The first composition is then cryopreserved to yield discrete cryopreserved self-sustaining bodies formed from the first composition in each of the wells.

The invention is also concerned with a method of forming a pooled preparation of cells. The method comprises providing a pre-pooled stack comprising (or consisting of) a plurality of discrete, cryopreserved self-sustaining bodies in a container. The self-sustaining bodies are formed from respective compositions of cells, wherein each of the respective compositions comprises cells from a different source (i.e., one composition comprises cells from one source, while another composition comprises cells from a different source). The stack is then thawed. Advantageously, upon thawing, the respective, formerly discrete compositions mix together to form a single composition comprising the cells from different sources, thereby creating the pooled preparation in situ in the container.

The invention also provides a receptacle or mold for forming cryopreserved compositions of cells into self-sustaining bodies. The receptacle comprises a surface and a plurality of wells defined in the surface thereof. The wells have respective widths and depths, wherein the width of each well is greater than the depth of each well. Advantageously, the surface of the receptacle is superhydrophobic (wetting resistance) allows a resting water droplet to exhibit a contact angle ($\theta_c$) of greater than about 90° at temperatures ranging from about −10° C. to about 50° C.

DETAILED DESCRIPTION

The present invention is directed towards cryopreservation for eventual pooling of cells, such as hepatocytes, blood cells, stem cells, pluri- and omni-potent cells, as well as cellular and subcellular fractions (e.g., organelles), including, but not limited to, mitochondria, cytosol, S9, and microsomes. For ease of reference, the term "cells," will be used generally herein to encompass both cells, as well as these cellular and subcellular fractions, unless the overall context indicates otherwise. The term "cryopreservation" is defined as processes where cells or whole tissues are preserved by cooling to low sub-zero temperatures (−90° C.) such that any biological activity is effectively stopped. The term "single-cryopreserved," as used herein, means that the cells have been subjected to a single instance of freezing (i.e., have not been thawed and refrozen). Terms such as "freezing" or "frozen" are used interchangeably herein with "cryopreservation" or "cryopreserve," and are defined herein to have the same meaning as cryopreservation.

Figure 1:
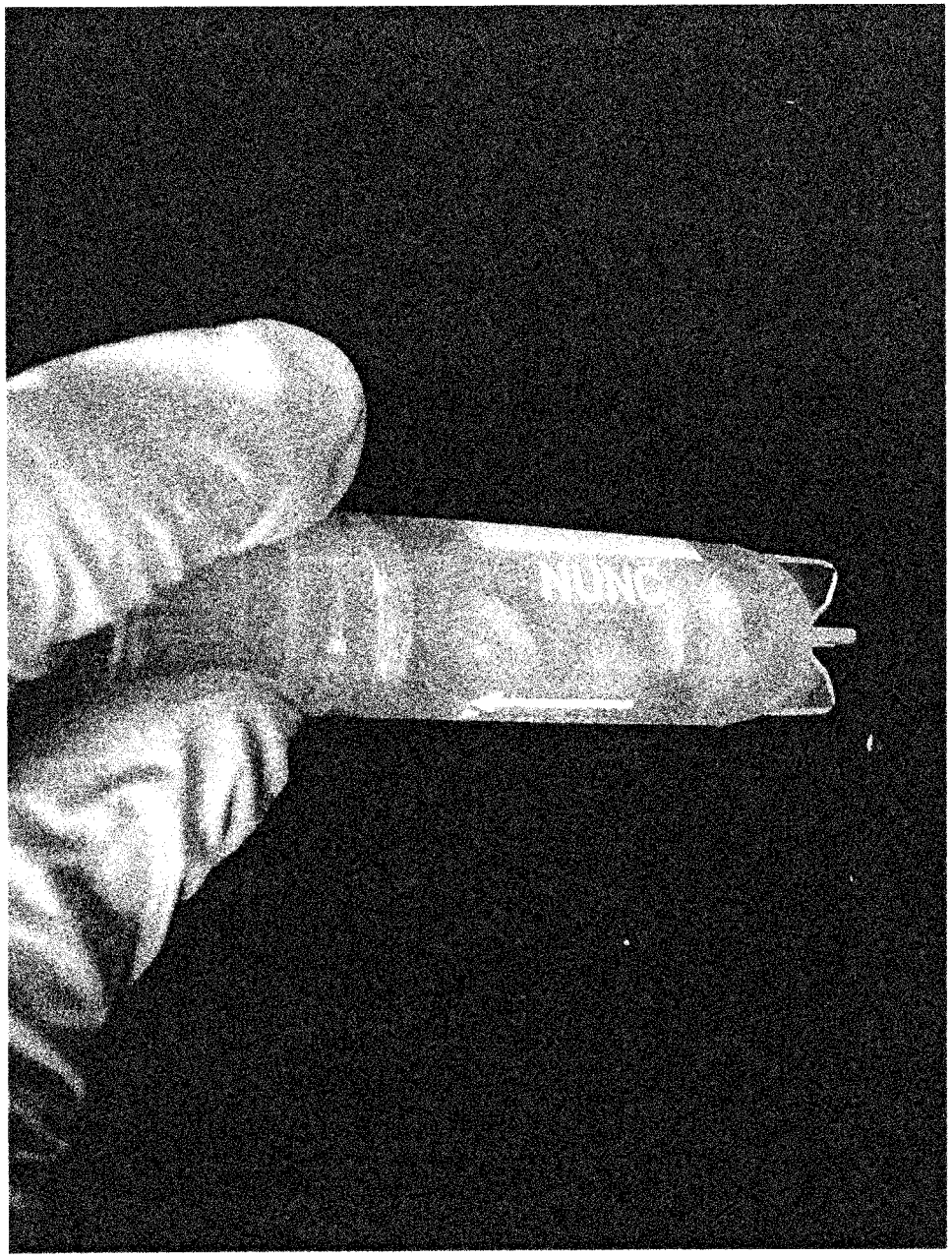
FIG. 1 is a photograph of the cryopreserved hepatocyte pellets from different sources collected in a vial for eventual thawing to create a single-cryopreserved pooled hepatocyte product from Example 2.

In the inventive method, a single-cryopreserved product is obtained. The cryopreserved products are cryopreserved compositions of cells in the form of a self-sustaining body. The term "self-sustaining body," as used herein, means that the cryopreserved composition of cells is a discrete, rigid (as opposed to a gel) body that maintains its shape in the cryopreserved state without a support structure and can be handled or moved independently of a container (such as a vial or well of the pellet mold). That is, self-sustaining means that contact can be made directly with the cryopreserved composition itself without the composition deforming or collapsing upon itself during handling. In one aspect, the self-sustaining bodies are provided in the shape of a pellet, as described herein. Single-cryopreserved products from different sources (e.g., different races, sexes, disease states, enzymatic activities) can be combined in their cryopreserved state to create a "pre-pooled" product, which, upon thawing, results in a pooled composition of cells from different sources. The term "pre-pooled" product, as used herein, refers to a combination of the single-cryopreserved products, each preferably from a difference source, wherein the single-cryopreserved products are combined or assembled in a single container (i.e., are stacked in physical contact with one another), but remain as discrete, self-sustaining, cryopreserved compositions (or pellets) of cells until thawing. That is, these discrete compositions of cells remain as separate and distinct bodies until thawing. FIG. 1 depicts a stack of pellets according to the invention. Advantageously, because such single-cryopreserved pellets remain discrete, self-sustaining bodies until thawing, they can be individually handled without a container, and can therefore be individually assembled into a stack in a vial, for example, with other pellets in any number of ways for eventual thawing into a pooled preparation. Thus, such pellets allow for easy customization of the eventual thawed, pooled products, because the contents of the pool do not have to be determined during the initial or subsequent cryopreservation steps as with traditional pooling methods, but can be decided upon post-cryopreservation, when the stack of selected cryopreserved pellets is assembled (i.e., the pools can be "made to order"). Each individual single-cryopreserved pellet can be, itself, from an individual (single) source or from a mixture of multiple sources, and can range in size anywhere from about 50 µL to about 2 mL, although about 100 µL is the preferred pellet volume. It will be appreciated that each individual pellet can contain also cells of more than one cell type, or even cells from different species (i.e., a single pellet could contain a mixture of blood cells and hepatocytes, or of human cells and mice cells, etc.).

A cell "source," as used herein, refers to obtaining cells from various donors, biopsies, tissue resections from different tissue samples or different tissue sources, different animals harboring cells (species), or primary, secondary, immortalized, or transformed cells. The cells may be derived from any mammalian source, including human, porcine, simian, canine, feline, bovine, equine, ovine, leporine, or murine sources, among others. Cells may be obtained from a single source at two or more different times, combined, and cryopreserved into a single pellet. Such cells would still be considered to be prepared from a "single source." Cells from different sources include those obtained from mammalian cells of different genders, genotypes, ages, races (e.g., Caucasian, etc.), enzymatic or metabolic activities, species, or disease or health states (e.g., hepatocytes of hepatitis virus-infected liver, hepatocytes of HIV-1 infected liver, hepatocytes of healthy liver, hepatocytes of cigarette smokers, hepatocytes of individuals suffering from cirrhosis of the liver, or from other diseases or conditions). Cells from different sources are particularly desired for producing pooled preparations. The terms "pooled" preparation or "pooling," as used herein, refer to a composition of cells that results from the combination of cells from more than one source, and generally comprises such cells suspended in a culture medium. The cells of such pooled preparations may be randomly selected, or may be specifically selected to provide the pooled preparation with a desired level of one or more metabolic activities (such as for example, a preparation of hepatocytes having a desired level of enzymatic activity, as described herein), or a desired cell characteristic (such as, for example, a preparation of hepatocytes derived from sources of a particular gender, genotype, age, race, or health state). For example, pooled hepatocyte preparations may be formulated so as to provide a preparation having the metabolic activities of an "average" hepatocyte sample or a preparation whose hepatocyte enzyme functions approximate the hepatocyte enzyme functions of freshly isolated hepatocytes. Such metabolic activities may include, for example, some or all of the following enzymatic activities: bupropion hydroxylase, amodiaquine N-dealkylase, diclofenac 4'-hydroxylase, coumarin 7-hydroxylase (COUM), dextromethorphan O-demethylase (DEX), 7-ethoxycoumarin O-deethylase (ECOD), mephenytoin 4-hydroxylase (MEPH), testosterone 6(β)-hydroxylase (TEST), tolbutamide 4-hydroxylase (TOLB), phenacetin O-deethylase (PHEN), chlorzoxazone 6-hydroxylase (CZX), or activities responsible for the phase II metabolism of 7-hydroxycoumarin (7-HCG (glucuronidase) and 7-HCS (sulfatase). The substrates, methods of measurements and assay units for assays of such metabolic activities are known in the art. The pre-pooled stack can also contain cells from different species, or of different cell types so that the resulting pooled preparation comprises cells of different species or of different cell types (i.e., a mixture of hepatocytes and blood cells, etc.).

In general, the cells are isolated from tissue, prepared for cryopreservation, cryopreserved, and then assembled into pre-pooled stacks, described above. These stacks can then be thawed to create pooled preparations. Cells for use in the inventive pellets and pooling method can be isolated according to any number of methods known in the art, including sedimentation and density gradient-based separation. In one aspect, enzymatic tissue dissociation is used to separate the cells from the extracellular matrix. Preferably, a perfusion technique, as described herein, is also used. Suitable enzymes for use in the digestion medium for tissue dissociation include collagenase types I and II, trypsin, hyaluronidase, protease, and pronase. The separated cells are then suspended in culture media, and preferably filtered. Suitable culture media for hepatocytes includes Chee's Essential Media, Modified Eagle Medium (or Dulbecco's Modified Eagle Medium (DMEM)), Leibowitz medium, Waymouth medium, Kreb's medium, and mixtures thereof, or supplemented versions thereof. Media may be supplemented with amino acids, FBS, antibiotics, antimicrobial agents, growth factors, micoelements (e.g., selenium), and mixtures thereof. Centrifugation and sequential washings can then be used to separate the target cell type from dead cells and other cell types (e.g., hepatocytes can be separated from dead and nonparenchymal cells). In particular, the cells collected from tissue dissociation can be subjected to centrifugation, followed by aspiration of the supernatant. The cell pellet can then be resuspended in culture media, preferably along with a density gradient medium. Density gradient media create a self-forming density gradient in the suspension facilitating separation and isolation of the target cells. Suitable density gradient medium is commercially available and includes PERCOLL® and FICOLL®. Density gradient medium is preferably diluted to an isotonic solution using a buffer solution, such as phosphate buffered saline (PBS), prior to use. After density gradient fractionation, the supernatant containing dead cells and other cell types can be aspirated away from the target cell pellet. The resulting isolated cells can then be washed in additional culture medium and centrifuged. Any methods known or available to one of ordinary skill in the art for isolation of cells may be used or adapted for the isolation of the cells used in the invention. For example, suitable techniques are outlined in Morisani et al. (ASAIO Journ. 41:155-161 (1995)) and in Selgen (Meth. Cell Biol. 13:29-83 (1976)). As an associated technique, a two-step collagenase procedure is also described in Li et al. (J. Tissue Cult. Meth. 14:139-146 (1992)).

To prepare the isolated cells for cryopreservation, the cells are preferably suspended in a culture medium comprising a cryoprotectant before being dispensed into the cryopreservation receptacle. The cryoprotectant minimizes the deleterious effects of cryopreservation, such as formation of intracellular ice. Suitable cryoprotectants are selected from the group consisting of fetal bovine serum (FBS), dimethyl sulfoxide (DMSO), polyethylene glycol, amino acids, propanediol, glycerol, and mixtures thereof. DMSO is particularly preferred for cryopreservation of hepatocytes. Other suitable cryoprotectants include Cryostor™ cryopreservation media, such as CS5 (5% DMSO), CS10 (10% DMSO), and CS2/DLite® (2% DMSO), available from BioLife Solutions®. For hepatocytes, the resulting suspension for cryopreservation preferably has a viable cell concentration of from about 1 million cells/mL to about 20 million cells/mL, more preferably from about 10 million cells/mL to about 15 million cells/mL, with about 12 million cells/mL being particularly preferred for human and rat cells (about 2 million being preferred for mouse cells). For subcellular fractions the viable concentration for cryopreservation preferably ranges from about 1 mg/mL to about 200 mg/mL, more preferably from about 10 mg/mL to about 50 mg/mL, with about 20 mg/mL being particularly preferred. The resulting suspensions are then dispensed into the pellet-forming receptacle for cryopreservation.

Cells are preferably frozen within about 36 hours after organ harvesting. However, it will be appreciated that a longer or shorter period of time between isolation of cells and subsequent cryopreservation is possible, and may be preferable or desirable, depending upon the cell preparation. For example, cells may be cryopreserved immediately after isolation, or as soon as reasonably possible after isolation (i.e., within 1 hour or less). Alternatively, cells may be cryopreserved after about 48 hours after isolation or longer. Cells may also be cryopreserved within about 6 to about 42 hours after isolation.

The pellet-forming receptacle preferably comprises a material that has the characteristics of physical flexibility, pliability, and resistance to breaking or cracking. The material used in forming the surface of the receptacle is preferably hydrophobic, and more preferably allows a resting water droplet to exhibit a contact angle ($\theta_c$) of greater than about 90°. The surface of the receptacle preferably has low chemical reactivity and thus is substantially "non-stick" to facilitate complete release of the pellets from the receptacle wells after cryopreservation, as described herein. Advantageously, because the pellets are completely released intact leaving behind no residue, the receptacle can then be reused. The material used to form the surface preferably has a very low coefficient of friction (and preferably less than about 0.5, more preferably less than about 0.1) at temperatures below zero degrees Celsius. More preferably, the material retains one or more of the foregoing characteristics at temperatures ranging between about −10° C. to about 50° C., and more preferably between about −5° C. and about 40° C. Suitable materials for forming the receptacle will comprise compounds selected from the group consisting of polytetrafluoroethylene (PTFE), perfluoroalkoxy (PFA), fluorinated ethylene-propylene (FEP), ethylene tetrafluoroethylene (ETFE), and combinations or copolymers thereof. Alternatively, the receptacle can be formed out of any suitable material (plastic, metal, etc.), and can simply comprise a coating of a hydrophobic film, such as films comprising a compound selected from the group consisting of polytetrafluoroethylene (PTFE), perfluoroalkoxy (PFA), fluorinated ethylene-propylene (FEP), ethylene tetrafluoroethylene (ETFE), and combinations or copolymers thereof. Particularly preferred examples of such materials include TEFLON® PFA, PTFE, FEP, and ETFE, available from DuPont™, Daikin Industries, and Solvay S. A.

Figure 6:
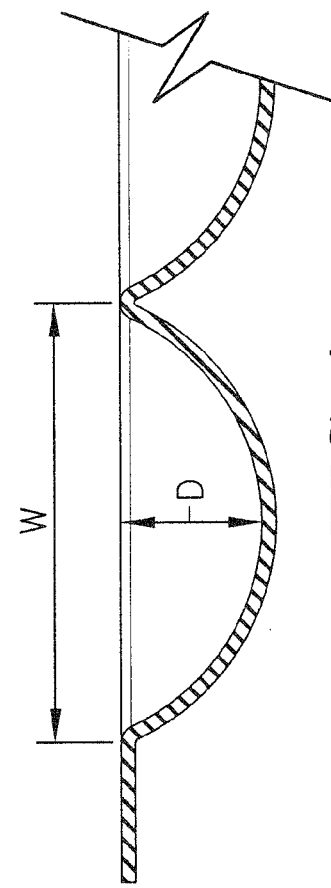
FIG. 6 is a fragmentary cross-section of the receptacle taken along line 6-6 in FIG. 4.

The receptacle comprises a plurality of depressions or "wells" defined in its surface for containing the individual cell suspensions. The wells serve as the mold for forming the discrete cell pellets during cryopreservation. The pellet receptacle can comprise from about 6 to about 1536 wells, more preferably from about 12 to about 384 wells, and even more preferably from about 24 to about 96 wells. The wells are preferably arranged in a rectangular matrix (1:1 or 2:3) across the receptacle surface. It will be appreciated that the size of the individual wells can vary; however, it is preferred that the width of each well is greater than its depth. As used herein, the term "width" (W) in reference to the wells refers to the maximum surface-to-surface dimension along the generally horizontal plane (i.e., width of a square, or diameter in the case of circular wells as shown in FIG. 6) when the receptacle is resting on a surface such as a table. Thus, the wells are preferably shallow. More preferably, the width, W, of the well is preferably at least about 2 times greater than the depth, D, of the well, more preferably at least about 2½ times greater than the depth of the well, and even more preferably at least about 2⅔ times greater than the depth of the well. For example, when the depth of the well is about 3 mm, the diameter of a circular well will be about 2⅔ times greater (or about 8 mm). With reference to FIG. 6, the width, W, of the wells preferably ranges from about 6 mm to about 20 mm, more preferably from about 6 mm to about 10 mm, and even more preferably from about 6 mm to about 8 mm. The depth, D, of the wells preferably ranges 3 mm to about 20 mm, more preferably from about 3 mm to about 15 mm, and even more preferably from about 3 mm to about 5 mm.

The receptacle can hold discrete aliquots of the same sample of isolated cells in each well. The receptacle can also hold multiple discrete aliquots of different samples of isolated cells, each in respective wells. Alternatively, a portion of the wells in the receptacle can be devoted to several aliquots of a single sample of isolated cells, while the remaining wells can be used to hold several aliquots of another sample or multiple samples of isolated cells. A single well could also hold an aliquot comprising cells from different sources (e.g., a mixture of cells). It will be appreciated that any combination of the same or different samples of cells can be combined on the receptacle. Likewise, the receptacle can contain aliquots in a single well, more than one well, or in all wells of the receptacle. The volume of each well will preferably range from about 20 μL to about 2 mL, more preferably from about 60 μL to about 2 mL, and even more preferably from about 110 μL to about 1 mL.

In use, aliquots of the cell suspensions prepared above are added to their respective wells, the receptacle is preferably covered with a lid, and then cryopreserved. Freezing volumes (i.e., volume of suspension in one well) can range from about 10 μL to about 2 mL. However, from about 50 μL to about 2 mL of the suspension is preferably added to each well, and more preferably from about 100 μL to about 1 mL, with about 100 μL of cell suspension per well being particularly preferred. Cryopreservation can be carried out using any method known in the art. Preferably, the cell suspensions are frozen using liquid nitrogen ($N_2$). A controlled rate freezing process is preferably used. More preferably, a freezing rate of from about −1° C./min. to about −25° C./min. is used until a final temperature of about −90° C. is reached. A latent heat release step can be included, wherein the sample temperature is increased slightly in the middle of the cryopreservation process. More preferably, the freezing rate is varied during the cryopreservation process. For example, the cell suspension is preferably cooled to a temperature of about 4° C., and then the temperature is decreased about −1° C./min. until a sample temperature of −4° C. is reached. The cell suspension temperature is then decreased at a rate of about −25° C./min. until the cryopreservation chamber reaches a temperature of about −40° C. A latent heat release step can be introduced wherein the temperature is then increased at a rate of about 15° C./min. until a temperature of about −12° C. is reached in the chamber. The temperature can then be decreased at a rate of about −1° C./min. until a chamber temperature of about −40° C. is reached. Finally, the temperature is decreased at a rate of about −10° C./min. until the chamber reaches −90° C. where it is maintained. A programmable freezing chamber can be used to facilitate cryopreservation.

After cryopreservation, the pellets can be stored under freezing (sub-zero ° C.) conditions in the receptacle itself, or can be removed from the receptacle and stored in another container. Suitable containers include vials ranging in size of from about 1 mL to about 50 mL, with about 1.5 mL to about 20 mL being particularly preferred. The frozen cell compositions are preferably stored in either the liquid $N_2$ ("$LN_2$") phase or the vapor phase of $LN_2$. The cells may be stored for virtually any length of time (days, months, years) with extended storage having little effect on post-thaw viability and function. To remove the pellets from the receptacle, the receptacle can simply be inverted over a collection container, and the backside of each well can be depressed to "pop" the pellets out of the wells. Alternatively, a blunt instrument (such as the backside of a spoon) can be used to slide the pellets out of the wells by pressing down on one side of the pellet thereby pushing and sliding the opposite side of the pellet upwards and out of the well. Although the size of the pellets can vary, the pellets preferably have an average thickness of from about 2 mm to about 15 mm, more preferably from about 3 mm to about 10 mm, and even more preferably from about 3 mm to about 5 mm. The pellets will preferably have an average width of from about 6 mm to about 20 mm, more preferably from about 6 mm to about 10 mm, and even more preferably from about 6 mm to about 8 mm. The term "width" as used herein with reference to the pellets means the maximum surface-to-surface dimension (e.g., the width of a square-shaped pellet, diameter of a circular pellet). As with the wells of the mold used to form the pellets, the pellets will preferably have a thickness that is less than the width of the pellet. Removal of the pellets is preferably carried out under freezing conditions (i.e., with the utensils and receptacle in the vapor phase of $LN_2$).

Advantageously, the resulting cryopreserved pellets are self-sustaining bodies that can be handled, manipulated, and moved via direct contact with the pellets, without a container and without the pellets deforming or collapsing under such contact and handling. Thus, the pellets can be stacked into a storage container for later use, and, at a later date, removed and individually assembled with other pellets from a different source of cells to create a "pre-pooled" stack of pellets of cryopreserved cell suspensions. The pre-pooled stacks comprise (or consist of) a plurality of the individual self-sustaining bodies. More specifically, the pre-pooled stacks can comprise (or consist of) from about 2 to about 100 of the individual self-sustaining bodies, and more preferably from about 10 to about 40 of the individual self-sustaining bodies, with stacks of 10 or 20 being particularly preferred. Each self-sustaining bodies can comprise cells from a single source or a mixture of sources. Thus, the stacks will preferably comprise multiple cell sources (e.g., a stack 10 can comprise 10 or more different sources). Unlike traditional pooled preparations, in which the pool is formed before cryopreservation, the present pre-pooled stack is formed in the cryopreserved state. One advantage of this is that traditional pooled preparations can only be removed from their respective containers upon thawing (i.e., they are frozen in and stuck to the vials). However, the inventive stacks comprise a plurality of self-sustaining bodies that are mobile and not stuck to their containers. Thus, stacks could be re-assembled if desired, or even combined with other stacks into a larger container depending upon the desired end use. The cryopreserved pellets may be thawed for use by removing them from freezing conditions, such as by removing them from the presence of $LN_2$ or the vapor phase of $LN_2$. Preferably, the pellets are thawed by placing the container of pellets (e.g., stacked pellets in a cryo vial, etc.) into a pre-warmed water bath or shaking water bath immediately after removing from freezing conditions. More preferably, the water bath has a temperature ranging from about 35° C. to about 40° C., with about 37° C. being particularly preferred, for about 0.1 to about 4 minutes, preferably from about 1 to about 2 minutes. It will be appreciated that the thawing time will depend upon the individual pellet size and the number of pellets in the stack. As the individual pellets thaw into their respective, thawed cell suspensions, these suspensions coalesce together (intermix) in the vial into a single pooled cell composition that forms in situ in the vial during thawing. Thus, the total volume of the thawed, pooled preparation will be equal to the sum of the individual pellet volumes in the container prior to thawing (e.g., a stack of ten 100-μL pellets will thaw into 1 mL of pooled preparation). Accordingly, for a pool of 10 to 20 pellets, the volume of the pooled preparation can range anywhere from about 100 μL to about 40 mL.

The contact between the thawed cells and the cryoprotectant at non-freezing temperatures is preferably minimized by quickly pouring the thawed contents into culture medium and centrifuging at room temperature or using density gradient fractionation to separate the cells from the cryoprotectant. The cryoprotectant, along with any fat or cell debris, is then removed with the supernatant. The resulting pooled cells are then resuspended in a culture medium. The centrifugation/resuspension process can be repeated, as desired. A portion of the suspension can also be removed for viability counting, described below.

After the desired number of resuspensions/centrifugations, cells can be resuspended in culture medium at the desired cell concentration. The resulting pooled preparation may then be used for medical research, pre-clinical testing, induction studies, and other purposes where pooled preparations are desirable. Advantageously, the cells in the pooled preparation have only be subjected to a single freeze-thaw cycle (i.e., a single instance of cryopreservation and thawing), minimizing cell damage as compared to traditional pooled preparations of multi-cryopreserved cells. There is no minimum or maximum amount of time necessary between freezing and subsequent thawing in the freeze-thaw cycle. It is particularly preferred that the cells for use in the invention be subjected to a single instance of cryopreservation. That is, the cells used to form the individual self-sustaining bodies (pellets) have preferably not been subjected to cryopreservation prior to the formation of the cryopreserved self-sustaining bodies, as described herein. Thus, the pooled cells have preferable not been frozen or thawed more than one time.

For pooled hepatocyte preparations, at least about 60% of the hepatocytes in the pooled preparation will be viable after thawing, more preferably at least about 70% of the hepatocytes in the pooled preparation will be viable, based upon the total recovered hepatocytes (identified via Trypan blue exclusion assay as viable) in the suspension taken as 100%. The pooled hepatocyte preparation can also be subjected to density gradient fractionation using a density gradient medium, such as PERCOLL®, to separate viable and non-viable cells, before viability counting. Preferably, at least about 60% of the hepatocytes in the pooled preparation will be viable after density gradient fractionation, and more preferably at least about 70% of the hepatocytes in the pooled preparation will be viable, based upon the total recovered hepatocytes (identified via Trypan blue exclusion assay) in the suspension taken as 100%. By way of a non-limiting example, viability can be determined using the Trypan Blue exclusion method described in the Examples. For example, a 50-μL aliquot of isolated cell suspension is mixed gently with a 400-μL aliquot of 1×PBS and a 50-μL aliquot of Trypan Blue. Cells can be counted using a hemocytometer and the percent viability and viable cell number is determined as described in the working Examples. References to cell "viability," as used to herein, refer to viability as assessed using the Trypan Blue exclusion method, unless indicated otherwise. Viability can be determined at a number of different points in the process, as desired, with or without density gradient fractionation being used in the process. Viability is preferably determined at least after initial isolation of the cells, before cryopreservation, and/or after thawing. Advantageously, the viability of a particular sample of pellets may be determined by simply removing one pellet from the storage container, thawing it as described, and determining viability. In this manner, the remaining pellets for that sample are undisturbed.

The pooled hepatocyte preparation will preferably have an enzymatic activity level similar to that of fresh hepatocytes. Thus, the pooled preparation will preferably have at least one enzymatic activity listed in Table 1 below falling within the listed ranges. That is, the pooled preparation does not necessarily have to meet the listed enzymatic activity for all twelve enzymes listed, but will preferably meet at least one or more. Alternatively, the pre-pooled stack can be assembled according to a user-defined profile to yield a pool that maximizes, minimizes, or emphasizes certain characteristics and functions over other functions, in which case the enzymatic activity may be outside one or all of the ranges defined below.

TABLE 1

| Enzyme Name | Marker substrate reaction | Broad Range[A] | Preferred Range[A] |
|---|---|---|---|
| CYP1A2 | Phenacetin O-dealkylation | 0-263 | 0-171 |
| CYP2A6 | Coumarin 7-hydroxylation | 0-165 | 0-104 |
| CYP2B6 | Bupropion hydroxylation | 0-172 | 0-116 |
| CYP2C8 | Amodiaquine N-dealkylation | 0-933 | 60-642 |
| CYP2C9 | Diclofenac 4'-hydroxylation | 0-678 | 143-500 |
| CYP2C19 | S-Mephenytoin 4'-hydroxylation | 0-42 | 0-27 |
| CYP2D6 | Dextromethorphan O-demethylation | 0-115 | 12-81 |
| CYP2E1 | Chlorzoxazone 6-hydroxylation | 0-658 | 33-449 |
| CYP3A4/5 | Testosterone 6β-hydroxylation | 0-1169 | 0-775 |
| CYP3A4/5 | Midazolam 1'-hydroxylation | 0-436 | 0-272 |
| UGT | 7-Hydroxycoumarin glucuronidation | 107-1030 | 338-799 |
| SULT | 7-Hydroxycoumarin sulfonation | 0-89 | 8-62 |

[A]pmol/million cells/min.

The pooled hepatocyte preparations prepared according to the inventive single-cryopreservation method have a number of uses. In particular, the pooled preparations can be used to investigate in vitro drug metabolism as well as study the affect and interaction of a xenobiotic (such as a drug, carcinogen, or pesticide) on the hepatocytes or their metabolic profile or individual enzymes. For example, after the pre-pooled stack is thawed creating the pooled preparation in situ, the pooled hepatocytes can be incubated in the presence of a xenobiotic. The metabolic fate of the xenobiotic or the affect of the xenobiotic on the hepatocytes or on an enzyme or metabolic activity thereof can then be determined.

EXAMPLES

The following examples set forth methods in accordance with the invention. It is to be understood, however, that these examples are provided by way of illustration and nothing therein should be taken as a limitation upon the overall scope of the invention.

Example 1

Isolation of Hepatocytes

A. Reagent Preparation

Various reagents for use in the following Example were prepared. To prepare about 20 L of 1-x Perfusion Buffer 1 (1x-PB1), the following reagents were dissolved in 18 L of high purity water: 137.9 g NaCl, 7 g KCl, 3.3 g $KH_2PO_4$, 42 g $NaHCO_3$, 19.8 g glucose, and 3.8 g ethylene glycol tetraacetic acid (EGTA). The pH was then adjusted to 7.4, as required, using 1-10 N NaOH or HCl at room temperature. Additional high purity water was added to reach a final volume of 20 L.

Next, 10 L of Perfusion Buffer 2 (PB2) was prepared by dissolving the following reagents in 9 L of high purity water: 69 g NaCl, 3.5 g KCl, 1.675 g $KH_2PO_4$, 21 g $NaHCO_3$, 10 g glucose, 2.2 g $CaCl_2$, and 1.45 g $MgSO_4$. The pH was adjusted to 7.4, as required, using 1-10 N NaOH or HCl at room temperature. The final volume was adjusted to 10 L using additional water. PB2 is combined with collagenase (Worthington Biochemical Corp., Freehold, N.J.; 90 units/mL).

The dexamethasone used in the Examples was prepared to a concentration of 10 mM in DMSO.

To prepare 20 L of DMEM for use in the Examples, the following reagents were dissolved in 18 L of high purity water: 267.2 g DMEM, 74 g $NaHCO_3$, 200 mL of 200 mM GlutaMAX-1, and 200 mL of 10 mM MEM Non-essential amino acids. The pH was adjusted to 7.4, as required, using 1-10 N NaOH or HCl at room temperature. The final volume was adjusted to 20 L using additional water. Supplemented DMEM (DMEM±) was prepared by dissolving the following reagents in 1 L of DMEM: 50 mL of 100% FBS, 1562 μL, of 4 mg/mL Insulin, 10 mL of 5,000 U/mL penicillin-5,000 μg/mL of streptomycin, and 100 μL, of 10 mM dexamethasone.

$DMEM^{+cryo}$ for use herein was prepared by adding the following reagents to 1 L of DMEM: 100 μL, of 10 mM hydrocortisone, 100 mL of 100% FBS, 1562 μL, of 4 mg/mL insulin, and 10 mL of 5,000 U/mL pennicillin-5,000 μg/mL streptomycin. The hydrocortisone used above was a stock concentration dissolved in DMSO.

B. In Situ Perfusion

Hepatocytes were isolated from an in situ human liver by a modification of the three-step collagenase perfusion method (Quistorff et al., *Preparation of isolated rat liver hepatocytes*, Methods in Molecular Biology, Vol. 5: Animal Cell Culture, pp. 151-160 (1989)).

The perfusion unit surfaces were cleaned and the chambers and perfusion lines were flushed with 70% v/v ethanol. The lines were then rinsed with 500 mL of sterile water, and primed with 1x-PB1. Next, the perfusion lines and bubble traps were filled with PB1. The animal was anesthetized with 50-60 mg/kg of a 50 mg/mL solution of sodium pentobarbital, and the liver was exposed. Cannulae were inserted into the portal vein and secured into place with suture silk. The liver was perfused using 1x-PB1 at 30-50 mL/min. for 9-15 minutes, followed by PB2 with collagenase at 50-60 mL/min. for 10-20 minutes, without recirculating.

Following perfusion, the flow rate was reduced to zero and the digested liver was carefully removed and placed into a sterile covered container and transported to a sterile hood where 35-45 mL of $DMEM^+$ was immediately added to the container. The hepatocytes were dispersed by tearing open Glisson's capsule (outer membrane) with the aid of sterile forceps and gently pulling apart the tissue until most of the cells were released into the medium. The cell suspension was then filtered through a 100-mesh nylon net (Spectrum) and collected in a sterile beaker. The container was then rinsed with 5-10 mL of $DMEM^+$, gently swirled to release any remaining cells, and filtered as before. If the perfusion and cell separation have been successful, only the vascular tree of the liver will remain on the filtration unit.

C. Perfusion of Excised Tissue

Hepatocytes were isolated from an excised human liver by a modification of the three-step collagenase perfusion method (Quistorff et al., *Preparation of isolated rat liver*

*hepatocytes*, Methods in Molecular Biology, Vol. 5: Animal Cell Culture, pp. 151-160 (1989)). The appropriate cannulae were inserted into one or more portal veins of the excised liver. The face of the liver was dry cut and the vessels were sealed using medical superglue, allowing 10 minutes for glue to set. The liver was then placed inside the perfuser unit and the perfuser inlet tubing was connected to one or more cannulae. The reservoir was filled with 1×-PB1, and the liver was perfused with 1×-PB1 at 50-300 mL/min. for 5-40 minutes, followed by PB2 with collagenase at 50-300 mL/min. for 10-25 minutes. Following perfusion, the digested liver was disconnected from the perfusion apparatus, the superglue, cannulae were removed, and 1-2 liters of DMEM$^+$ was added. The liver was teased apart using sterilized surgical scissors and forceps (or other appropriate instruments). As needed, additional DMEM$^+$ was added to the hepatocytes and the cell suspension was then filtered through a stainless steel filtration unit (BCS™) or two layers of cheesecloth and collected in a sterile container.

D. Hepatocyte Isolation

For both in situ and excised liver perfusions, the hepatocytes were then transferred to a sterile centrifuge tube and centrifuged at 55-140 RCF for 5 minutes at room temperature (~15-25° C.). The supernatant fraction was discarded, and the cell pellet was gently resuspended in 5-10 ml of DMEM$^+$ by inverting the tube several times. A volume of 90% isotonic PERCOLL® (1:9 v/v 10 PBS:PERCOLL) was added to the suspension to reach a final PERCOLL® concentration of 15-25% v/v for hepatocytes isolated from primates, humans, dogs, or pigs. The cell suspension (containing PERCOLL®) was mixed gently by inversion and then subjected to centrifugation at 55-140 RCF for 5±2 minutes at room temperature. Dead hepatocytes and remaining nonparenchymal cells in the supernatant were aspirated out and discarded, and the cell pellet was resuspended with 5-10 ml of DMEM+. The hepatocyte suspensions can be combined into larger lots if desired. The cells were then gently washed in DMEM$^+$ by centrifugation at 50-140 RCF for 3±2 minutes at room temperature. The final cell pellet was gently resuspended in culture medium containing 5-10% DMSO to form a hepatocyte suspension at a concentration of about 10-20 million cells/mL.

E. Cell Number and Viability

Cell number and viability can be calculated by diluting an aliquot of the cell suspension 8:1:1 (v/v/v) with PBS, pH 7.4, and 0.04% (w/v) Trypan Blue, and counting the cells in a hemocytometer. Each large square of the hemocytometer, with cover slip in place, represents a total volume of 0.1 mm$^3$. The nuclei of damaged cells stain blue when viewed under bright field optics. Healthy cells appear spherical without surface "blebs." Viability was determined by dividing the number of healthy cells by the total number of cells counted.

Example 2

Preparation and Pre-Pooling of Cryopreserved Hepatocyte Pellets

A. Cleaning, Autoclaving and Assembling of the Pellet Holder

Pellet holder assembly consists of pellet holder base, pellet holder (cryopreserved pellet receptacle, see Example 3) and the lid.

1. The pellet holder base (a sturdy 96-well base made of plastic, that the pellet holder is placed on during the cryopreservation process) and lid (a molded plastic top that fits over the top of the pellet holder and pellet holder base that enables sterility during the cryopreservation process) were cleaned using mild soapy water, then rinse with tap water, followed by deionized water;

2. The pellet holder was cleaned by placing the pellet holder in a 1 L beaker and filling to the level of the holder wells with acetone;

3. The pellet holder was sonicated for ~10-15 min;

4. The acetone was washed off with warm soapy water, and the pellet holder was rinsed first with tap water, then with deionized water;

5. The pellet holder was assembled onto the pellet holder base, and placed in an autoclave bag;

6. The pellet holder lid was placed in a separate autoclave bag; and

7. All parts were autoclaved at 125° C. and 15 psi for 25 min.

B. Preparation for Cryopreservation

1. A suspension of isolated hepatocytes prepared in Example 1 above was obtained.

2. The percentage and number of viable hepatocytes was then determined and recorded, if desired.

3. The cell suspension was centrifuged at 40-80×g for 2-5 minutes at 10 to 30° C.

4. The supernatant fraction was aspirated and discarded, followed by resuspension of the resulting cell pellet in culture medium containing 5-10% DMSO to a cell concentration of approximately 10-15 million cells/mL.

C. Cryopreservation and Storage of the Pellets

1. In a sterile hood, the autoclave bag was opened and the sterilized pellet holder base and the pellet holder were removed;

2. The pellet holder and its base were placed on ice;

3. 100 µL of the hepatocyte suspension prepared above was added to each well, using a multi-channel pipettor;

4. The sterilized lid was placed on top of the pellet holder;

5. The pellet holder was transferred from the sterile hood to the cryopreservation freezing chamber, on ice;

6. The hepatocyte suspensions were cryopreserved using a programmable freezing chamber according to the following program:

| Section Number | Rate of temperature change | Event to end the section |
| --- | --- | --- |
| 1 | Cool chamber and sample to 4° C. | Hold until manually advanced |
| 2 | −1° C./minute | −4° C. sample temperature |
| 3 | −25° C./minute | −40° C. chamber temperature |
| 4 | +15° C./minute | −12° C. chamber temperature |
| 5 | −1° C./minute | −40° C. chamber temperature |
| 6 | −10° C./minute | Hold at −90° C. chamber temperature |
| 7 | | End |

Suitable programmable cryopreservation freezers include: CryoMed Controlled Rate Freezers and Thermo Electron Cryomed Controlled Rate Freezers, both by Thermo Fisher Scientific.

7. While freezing, a Styrofoam box was filled with $LN_2$ and the utensils (tray, forceps, 50 mL conical tubes, and trough) were placed inside of box, but not immersed in the $LN_2$. All items were maintained in the vapor phase of the liquid $N_2$;

8. Once the freezing program was finished, the pellet holder assembly was removed and the cryopreserved pellets were quickly popped out of pellet holder (this can be done with either an inverted spoon or with gloved hands depressing the backside of the wells and sliding the pellets out) into the trough;

9. The cryopreserved pellets were transferred into a 50-mL conical tube and labeled;

10. The 50-mL conical tube containing the pellets was placed into the vapor phase of a $LN_2$ Dewar for storage.

D. Pre-Pooling of the Cryopreserved Pellets

Figure 2:
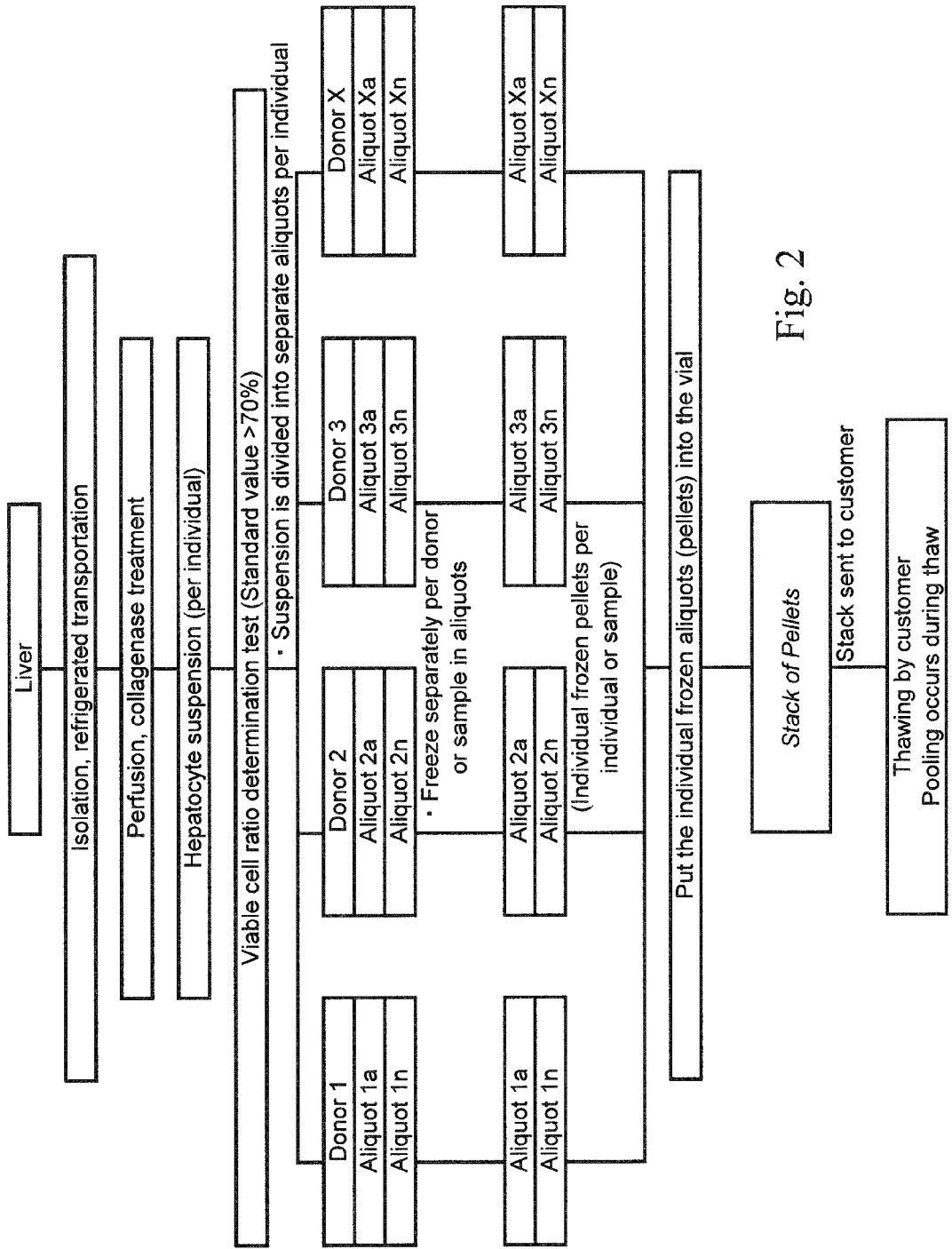
FIG. 2 is a flowchart of a method of making single-cryopreserved hepatocytes where pooling occurs during thawing for the first time from Example 2.

1. A large Styrofoam box was filled with $LN_2$;

2. The pre-labeled, sterile and uncapped cryo vials (Nunc; Thermo Fisher Scientific; Rochester, N.Y.) as well as the forceps, and a trough were placed inside the box in the vapor phase of $LN_2$;

3. The conical tubes containing the selected groups of cryopreserved pellets were transferred from the storage location into the vapor phase of $LN_2$ in the Styrofoam box;

4. Using pre-cooled forceps, selected cryopreserved pellets were removed from the conical tubes into each cryo vial (e.g., one pellet in each vial);

5. The remaining pellets were placed back into conical tube and put back in the storage Dewar;

6. Steps 3-5 were repeated for the other selected cryopreserved pellet samples (donors) to form the desired "pre-pooled" stack of pellets;

7. Once the desired stack of cryopreserved pellets had been assembled in the cryo vials, the caps are replaced on the cryo vials. FIG. 1 shows a photograph of the resulting stack in a Nunc cryo vial;

8. The cryo vials containing pre-pooled pellet stacks were then stored in the vapor phase of $LN_2$ until use. This process is also depicted in the flowchart in FIG. 2.

Example 3

Thawing and In Situ Pooling of Cryopreserved Hepatocytes

To thaw the pre-pooled pellet stacks, a cryo vial containing the selected stack was removed from the vapor phase $N_2$ storage unit and quickly placed into a prewarmed shaking water bath (37±1° C.) so that the level of the water bath was above the high point of the top pellet in the stack. The pooled hepatocyte composition was formed in situ, as the individual pre-pooled pellets thaw and the formerly discrete, frozen suspensions mixed together into a single pooled hepatocyte composition in the cryo vial. For example, a stack of 10 discrete 100 µL, pre-pooled pellets thawed into 1 mL of pooled hepatocyte composition. Once thawed, the cryo vials were quickly removed from the water bath, and their contents were gently poured into a vial containing DMEM$^{+cryo}$ (about 3-5 times volume of the pellet stack) and IsoPercoll (90% PERCOLL® in 10×PBS). The cryo vial was then rinsed with 1.5 mL of DMEM+, which was added to the pooled product, and gently mixed by inversion.

The pooled suspension was centrifuged at 60-120×g for 5 minutes±15 seconds at room temperature, and then the supernatant was aspirated and discarded. Any fat or cell debris in the supernatant fluid was also removed. A small amount (3-5 times post-centrifugation cell pellet volume) DMEM$^{+cryo}$ was then added, if necessary, to gently resuspend the cells by inversion.

An aliquot of the pooled hepatocyte suspension was removed for viability counting using Trypan-blue exclusion analysis (see below) and an 8:1:1 ratio of 1×PBS, Trypan blue, and cell suspension. For example, a 50 µL, aliquot of suspension was mixed gently with a 400 µL, of 1×PBS and 50 µL, of Trypan blue. The cells were counted using a hemocytometer, as described.

The cell viability was calculated by the following equation:

$$Vc \div Tc \times 100 = \% \text{ Viability}$$

Vc=# of viable cells counted in the hemocytometer

Tc=total # of cells (viable+nonviable) counted in the hemocytometer

Percent viable recovery can be calculated using the following equation:

$$TVc \div CVc = \% \text{ Viable Cell Recovery}$$

TVc=# of total viable cells in thawed suspension

CVc=# of cryopreserved viable cells removed from cryo-storage.

Viability may, alternatively, be determined after the second centrifugal pelleting of the cells, instead of after the first centrifugal pelleting.

Next, DMEM$^{+cryo}$ was added to obtain a cell concentration of approximately 1 to 4×10$^6$ cells/mL. The resulting suspension was centrifuged at 40-60×g for 3 minutes±15 seconds at room temperature. The supernatant was then aspirated and discarded. The cell pellet was then resuspended in the media of choice (e.g., DMEM$^{+cryo}$, Waymouth's+, Krebs-Henseleit Buffer, etc.) by inversion. The volume of the pooled cell suspension was measured and q.s. to the desired volume to bring the cells to the desired concentration.

Example 4

Enzymatic Activity and Marker Substrate Reactions

The enzymatic activity and marker substrate reactions of the pooled hepatocyte suspensions prepared according to the procedures in Examples 1-3 were determined. A stack of ten 100 µL, pellets (1 mL total) according to the invention, one each from a different donor (10 donors), was used for analysis. All donors were HIV, HBV, HCV, and HTLV negative and between 32 and 76 years of age. Six of the donors were positive for CMV, while 4 of the donors were negative. Seven of the donors were Caucasian, 1 donor was Hispanic, and the remaining 2 donors were of other races. Causes of death among the donors included: anoxia, head trauma, and cerebrovascular accident. The viability and activity post-PERCOLL® density gradient fractionation (isopycnic centrifugation) for the pooled stack was compared to the viability and activity of the individual pellets from each donor sample. The inventive pool was also tested for UGT and SULT activity, while the individual hepatocyte pellets were not. The enzyme names and marker substrate reactions are listed in Table 2 below. The results are found in Table 3.

TABLE 2

| Enzyme Names | Marker substrate reactions (pmol/million cells/min.) |
|---|---|
| CYP1A2 | Phenacetin O-dealkylation |
| CYP2A6 | Coumarin 7-hydroxylation |
| CYP2B6 | Bupropion hydroxylation |
| CYP2C8 | Amodiaquine N-dealkylation |
| CYP2C9 | Diclofenac 4'-hydroxylation |
| CYP2C19 | S-Mephenytoin 4'-hydroxylation |
| CYP2D6 | Dextromethorphan O-demethylation |
| CYP2E1 | Chlorzoxazone 6-hydroxylation |
| CYP3A4/5 | Testosterone 6β-hydroxylation |
| CYP3A4/5 | Midazolam 1'-hydroxylation |
| UGT | 7-Hydroxycoumarin glucuronidation |
| SULT | 7-Hydroxycoumarin sulfonation |

TABLE 3

| Individual Samples Donor # | Cell Yield (per 100 μL or 1 pellet) | Post-Percoll Viability (%) | 1A2 (ACE) | 2A6 (OCM) | 2B6 (OBP) | 2C8 (DAQ) | 2C9 (ODC) | 2C19 (4OMP) | 2D6 (ODX) | 2E1 (OCZ) | 3A4/5 (6OT) | 3A4/5 (1OM) |
|---|---|---|---|---|---|---|---|---|---|---|---|---|
| 1 | 1,250,000 | 78.6 | 12.2 | 33.5 | 35.6 | 415 | 208 | 1.76 | 54.5 | 255 | 1.1 | 14.4 |
| 2 | 1,010,000 | 84.0 | 71.8 | 2.12 | 27.8 | 233 | 631 | 27.8 | 69.1 | 300 | 875 | 141 |
| 3 | 117,000 | 73.8 | 8.13 | 21.3 | 8 | 36.2 | 69.8 | 7.02 | 24.5 | 55.7 | 38.2 | 7.54 |
| 4 | 584,000 | 74.4 | 4.76 | 94.1 | 109 | 66.7 | 154 | 0.943 | 20.7 | 98.6 | 29.2 | 6.97 |
| 5 | 682,000 | 86.8 | 17.4 | 10.1 | 10.6 | 368 | 394 | 0.65 | 188 | 378 | 15.1 | 10.9 |
| 6 | 488,000 | 78.5 | 92.9 | 109 | 165 | 298 | 259 | 2.3 | 8.97 | 168 | 381 | 55.8 |
| 7 | 390,000 | 78.8 | 38.2 | 18.8 | 143 | 435 | 276 | 2.84 | 60.6 | 123 | 323 | 39.4 |
| 8 | 1,040,000 | 85.4 | 38.3 | 4.46 | 18.1 | 187 | 396 | 4.55 | 55.5 | 248 | 166 | 72.4 |
| 9 | 1,120,000 | 70.0 | 78.1 | 9.43 | 14 | 223 | 386 | 1.93 | 64.7 | 225 | 62.3 | 16.9 |
| 10 | 400,000 | 72.0 | 29.4 | 17.3 | 50.7 | 192 | 244 | 1.66 | 35.7 | 140 | 166 | 19.6 |
| Avg. | 708,100 | 78.23 | 39.119 | 32.011 | 58.18 | 245.39 | 301.78 | 5.1453 | 58.227 | 199.13 | 205.69 | 38.491 |
| Pool of 10 Pellets | — | 75.20 | 53.1 | 18.1 | 68.5 | 315 | 325 | 4.9 | 55.2 | 278 | 213 | 48.5 |

As can be seen from the results in Table 3 above, the pre-pooled, single-freeze, pelleting method of preparing pooled hepatocytes preserves the activity of the cells' drug metabolizing enzymes. The enzymatic activities for the pooled preparation of 10 pellets closely resemble that seen across the individual donors. The enzymatic activity for UGT and SULT for the pool was 734 and 88.2 pmol/million cells/min., respectively.

The above procedure was repeated using a stack of twenty 100 μL pellets (2 mL total), one each from a different donor (20 donors). In the pool of 20, all donors were negative for HIV, HBV, HCV, and HTLV, and ranged in age from 32-72 years old. Of the 20 donors, 16 were positive and 4 were negative for CMV. Thirteen of the donors were Caucasian, 3 were African American, 2 were Hispanic, 1 was Indian, and 1 was Pacific Islander. Causes of death among the donors included: anoxia, head trauma, cerebrovascular accident, and aortic aneurysm. The results are found in Table 4 below.

pooled hepatocytes preserves the activity of the cells' drug metabolizing enzymes. The enzymatic activities for the pooled preparation of 20 closely resemble that seen across the individual donors.

Figure 3:
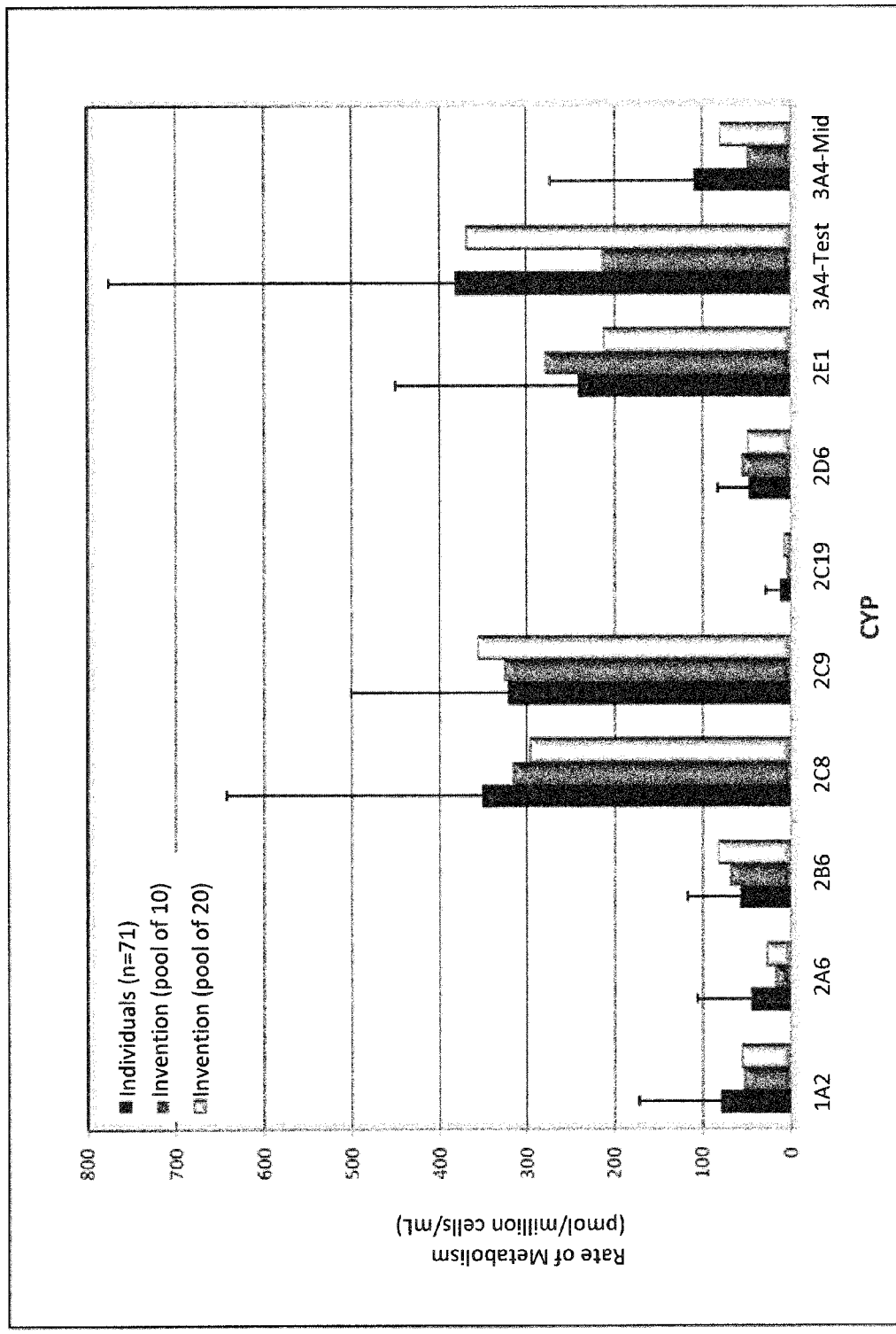
FIG. 3 is a graph showing the results of the enzymatic activity comparison of the inventive single-cryopreserved pooled hepatocyte products (n=10) and (n=20) with 71 individual human donor lots (n=71) cryopreserved using traditional cryopreservation methods from Example 4.

Next the activity of the each inventive pool was compared to the mean enzymatic activities from 71 individual human donor lots (n=71) cryopreserved using traditional cryopreservation methods (individual 1.5 mL samples cryopreserved in cryo vials). The individual lots were each measured in triplicate. As can be seen from the results in FIG. 3, the enzymatic activities of the inventive pooled product closely resemble that seen across individual donors. The error bars show the extent of inter-individual variance. These results demonstrate that the smaller freezing volume of the individual pellets (100 μL), as compared to the larger freezing volume of the traditional preparation (1.5 mL) preserves equally well the enzymatic activity of the cells. In addition, it can be seen that the manipulation of the self-sustaining pellets to form the pre-pooled stack (removal

TABLE 4

| Individual Samples Donor # | Cell Yield (per 100 μL or 1 pellet) | Post-Percoll Viability (%) | 1A2 (ACE) | 2A6 (OCM) | 2B6 (OBP) | 2C8 (DAQ) | 2C9 (ODC) | 2C19 (4OMP) | 2D6 (ODX) | 2E1 (OCZ) | 3A4/5 (6OT) | 3A4/5 (1OM) |
|---|---|---|---|---|---|---|---|---|---|---|---|---|
| 1 | 1,250,000 | 78.6 | 12.2 | 33.5 | 35.6 | 415 | 208 | 1.76 | 54.5 | 255 | 1.1 | 14.4 |
| 2 | 1,010,000 | 84.0 | 71.8 | 2.12 | 27.8 | 233 | 631 | 27.8 | 69.1 | 300 | 875 | 141 |
| 3 | 117,000 | 73.8 | 8.13 | 21.3 | 8 | 36.2 | 69.8 | 7.02 | 24.5 | 55.7 | 38.2 | 7.54 |
| 4 | 584,000 | 74.4 | 4.76 | 94.1 | 109 | 66.7 | 154 | 0.943 | 20.7 | 98.6 | 29.2 | 6.97 |
| 5 | 682,000 | 86.8 | 17.4 | 10.1 | 10.6 | 368 | 394 | 0.65 | 188 | 378 | 15.1 | 10.9 |
| 6 | 488,000 | 78.5 | 92.9 | 109 | 165 | 298 | 259 | 2.3 | 8.97 | 168 | 381 | 55.8 |
| 7 | 390,000 | 78.8 | 38.2 | 18.8 | 143 | 435 | 276 | 2.84 | 60.6 | 123 | 323 | 39.4 |
| 8 | 1,040,000 | 85.4 | 38.3 | 4.46 | 18.1 | 187 | 396 | 4.55 | 55.5 | 248 | 166 | 72.4 |
| 9 | 1,120,000 | 70.0 | 78.1 | 9.43 | 14 | 223 | 386 | 1.93 | 64.7 | 225 | 62.3 | 16.9 |
| 10 | 400,000 | 72.0 | 29.4 | 17.3 | 50.7 | 192 | 244 | 1.66 | 35.7 | 140 | 166 | 19.6 |
| 11 | 576,000 | 82.3 | 33.5 | 3.07 | 42.5 | 83.3 | 501 | 10.8 | 57.4 | 206 | 129 | 23.4 |
| 12 | 500,000 | 86.0 | 40.7 | 7.07 | 13.9 | 97 | 157 | 11.1 | 27.3 | 122 | 227 | 38.2 |
| 13 | 524,000 | 73.4 | 43.6 | 98.6 | 329 | 560 | 388 | 2.7 | 47.6 | 469 | 326 | 56.9 |
| 14 | 360,000 | 71.0 | 257 | 102 | 407 | 399 | 455 | 4.36 | 94.2 | 76.5 | 1550 | 478 |
| 15 | 510,000 | 79.2 | 29.8 | 10.9 | 222 | 271 | 684 | 3.18 | 98 | 161 | 420 | 71.5 |
| 16 | 376,000 | 70.5 | 62.9 | 53 | 29.5 | 206 | 235 | 8.76 | 30.1 | 145 | 499 | 50.2 |
| 17 | 1,100,000 | 76.0 | 58 | 8.8 | 67.4 | 341 | 548 | 6.57 | 50.4 | 399 | 40.9 | 6.57 |
| 18 | 437,000 | 89.5 | 96.1 | 71.1 | 17.2 | 284 | 340 | 64.4 | 29.7 | 210 | 744 | 76.7 |
| 19 | 245,000 | 92.4 | 73 | 125 | 274 | 268 | 333 | 19.1 | 81.8 | 116 | 1240 | 274 |
| 20 | 587,000 | 69.9 | 30.9 | 60.1 | 171 | 435 | 502 | 24.5 | 49.9 | 135 | 377 | 71.7 |
| Avg. | 614,800 | 78.625 | 55.8 | 43.0 | 108 | 270 | 358 | 10.3 | 57.4 | 202 | 380 | 76.6 |
| Pool of 20 Pellets | — | 73.8 | 53.9 | 26.5 | 81.2 | 295 | 355 | 7.41 | 46.9 | 211 | 367 | 78.5 |

As can be seen from the results in Table 4 above, the pre-pooled, single-freeze, pelleting method of preparing from receptacle and assembly of stack), as compared to the handling of the vials containing the traditional preparations (where no actual contact with the cryopreserved preparation itself occurs), was done in a way that protects the enzymatic activity of the cells.

Example 5

Pellet Holder Receptacle

Figure 4:
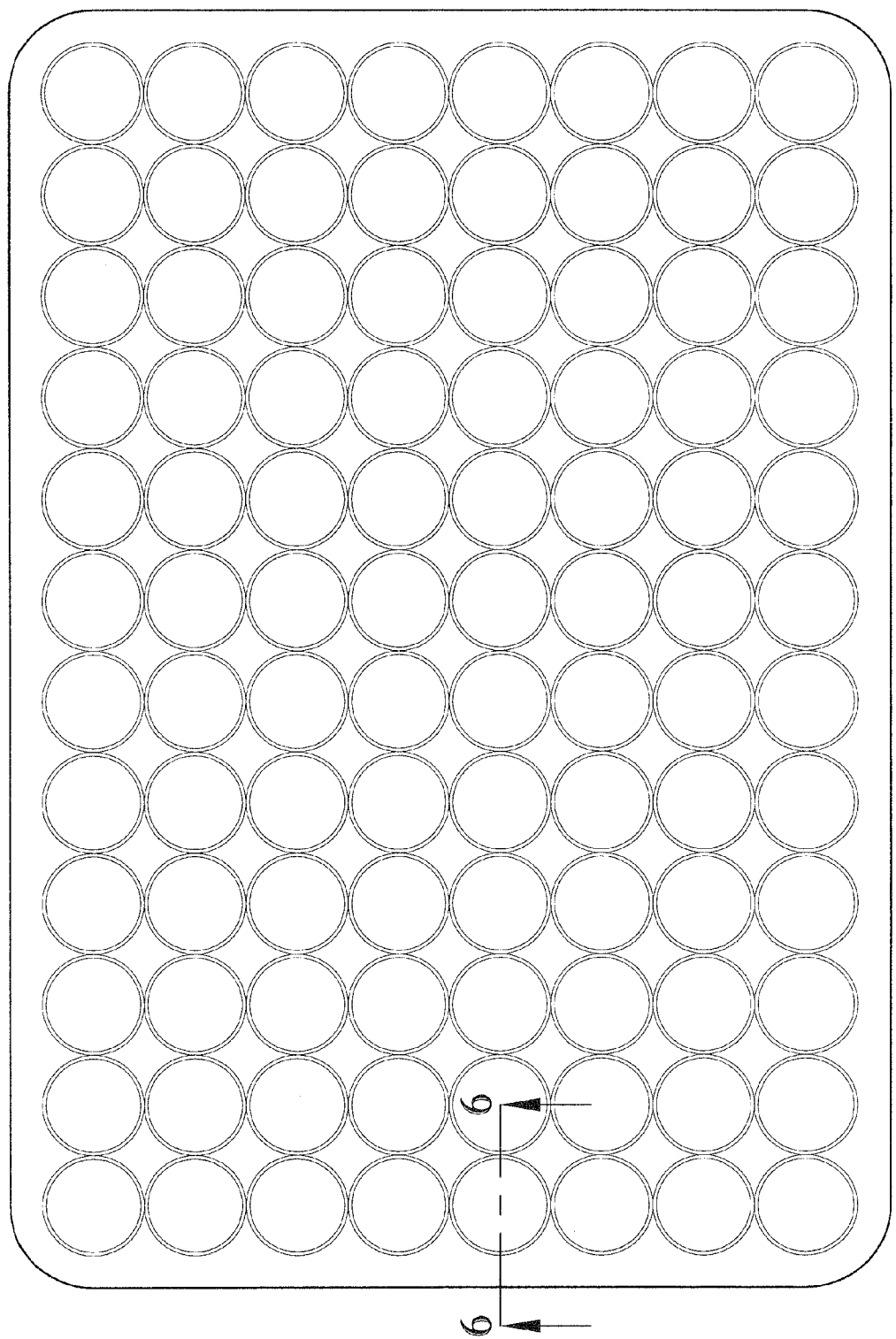
FIG. 4 illustrates a receptacle created according to Example 5.
Figure 5:
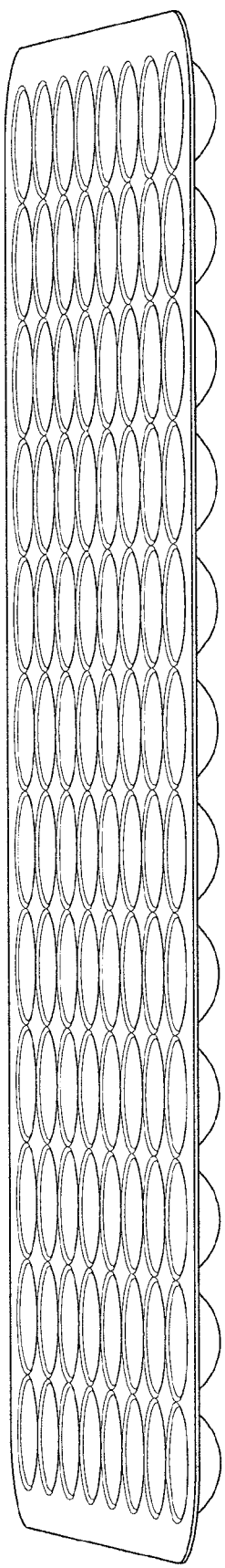
FIG. 5 depicts a side elevation view of the receptacle from FIG. 4.

In this Example, a pellet holder used to form the cryopreserved pellets according to Example 2 was prepared. A 0.005-inch thick film of TEFLON® PFA or PTFE (both from DuPont™) was cut into 100 mm×140 mm sheets. A 96-well microtiter plate (DeepWell™; Nunc) was used as the mold form. For the mold ram, or positive die forming tool, a standard 96-well plate cover was modified using bearing balls having a diameter of 7/32 inches inserted in the positions corresponding to each well of the plate. A clean and defect free sheet of TEFLON® PFA or TEFLON® PTFE was attached to the mold form (covering the wells) using 14 mm-wide laboratory grade tape. Using a hand-operated press, the plate was then pressed into the sheet so that the impression of the ball bearings was pressed into the TEFLON® PFA or TEFLON® PTFE sheet to form depressions in the sheet corresponding to the plate wells. This process was repeated multiple times, while the assembly of the mold form, TEFLON® sheet, and die forming tool was rotated 90 degrees between application of the compressing force. The resulting TEFLON® PFA or TEFLON® PTFE film-based multi-well pellet receptacle can hold up to 96 pellets. See FIGS. 4-6. It will be appreciate that this method can be used to form pellet receptacles of virtually any size. An automated pressing force could also be used.

Example 6

Subcellular Fractionation and Pooling

The procedure used to prepare subcellular fractions was based on the method of Salach and Weyler (Preparation of the flavin-containing aromatic amine oxidase of human placenta and beef liver. *Methods Enzymol.* 142: 627-637, 1987), where cells were lysed and subcellular components are separated by a series of centrifugations at increasing speeds. Following each successive centrifugation, the organelles that have sedimented to the bottom were recovered. The supernatant was then recentrifuged at higher speeds to sediment the next-largest organelles. Although mitochondria was used in the present Example, it will be appreciated that other organelles may be separated according to the same basic procedure. Mitochondria were prepared from fresh liver samples or from liver samples previously frozen in an ultra-low freezer (−70° C. or below), or in liquid nitrogen ($N_2$) or Freon and stored at −70° C. or below.

Livers were homogenized in homogenization buffer (50 mM Tris.HCl, pH 7.4 at 4° C. containing 150 mM KCl and 2 mM EDTA). Approximately, 2 or 3 mL of homogenization buffer were used per gram of wet liver weight to give a 33-25% homogenate, respectively. The homogenate was subjected to centrifugation at 400-500 gmax for 15±1 minutes at 0-8° C. to remove cell debris and nuclei. The supernatant fraction was then subjected to centrifugation at 12,000-13,000 gmax for 15±1 minutes at 0-8° C. to separate the mitochondria (pellet) from the S9 fraction (supernatant). The initial crude mitochondrial pellet was resuspended in wash buffer (10 mM EDTA containing 150 mM KCl), and re-isolated by centrifugation at 7,500-8,000 gmax for 15±1 minutes at 0-8° C.

This procedure (resuspension and centrifugation) was then repeated. After the final wash, the pellet was resuspended in a small volume of 250 mM sucrose (e.g., 0.5 mL of 250 mM sucrose per gram of wet liver weight) to give a protein concentration of approximately 10-40 mg protein/mL. The suspension was dispensed into respective wells of a sterilized pellet holder for cryopreservation, and cryopreserved, as described above. The cryopreserved pellets can then be assembled into pre-pooled stacks.

A. Detailed Procedure

1. Liver weighed and weight recorded (typically to within 0.1 g).

2. The liver was place din an appropriately sized beaker or Potter-Elvehjem-type mortar (i.e., one large enough to hold liver and buffer without reaching the maximum permissible volume). The frozen liver was thawed in room temperature homogenization buffer (2 or 3 mL of homogenization buffer per gram of liver) and then placed on ice, resulting in 33 to 25% homogenate, respectively. The ratio of homogenization buffer to liver may be increased without affecting the quality of mitochondria. Decreasing the amount of buffer (less than 1.5 mL per gram of liver) may result in contamination of the mitochondria by other organelles.

3. The initial homogenization was performed with a Polytron, steel-blade homogenizer. When more than one mitochondrial sample was being prepared, the blade was rinsed with water and excess was wiped off with paper towels (or equivalent) before switching to the next sample. The liver was homogenized with two or three 5-10 second intervals (or more if larger volume) with a Brinkman Polytron homogenizer (Model PT 10-35 [Polytron PTA 20-TS] with PCU-11 power supply, Kinematica GmbH, Luzern, Switzerland). A Vibracell Sonicator or equivalent was used for tissue that is more difficult to homogenize. Typically, two or three 5-10 second intervals is needed.

4. The liver was then homogenized with 3-8 passes of a relatively loose fitting TEFLON® pestle with a motor-driven homogenizer (e.g., Caframo stirrer Type RZR50, Wharton, Ontario, Canada) The homogenization tubes were returned to ice for at least one minute to cool the liver homogenate to ~4° C. If more than one mitochondrial sample is being prepared, Teflon pestle was rinsed or wiped off with paper towels (or equivalent) before switching to the next sample.

5. Step 4 was then repeated making sure to allow the homogenate to cool on ice for at least one minute. (The step can be repeated 2-3 more times as needed.)

6. The homogenate was then transferred to low speed centrifuge tubes. Pairs were balanced and placed opposite each other in a pre-cooled rotor. Unbroken cells and nuclei were removed from the homogenate by centrifugation at 400-500 gmax for 15±1 minutes at 0-8° C. The supernatant fraction containing mitochondria, microsomes and cytosol was transferred to another centrifuge tube and the pellet containing cell debris and nuclei was discarded.

7. The supernatant fraction was then centrifuged at 12,000-13,000 gmax for 15±1 minutes at 0-8° C. to separate the mitochondria (pellet) from the S9 fraction (supernatant). The postmitochondrial supernatant (S9 fraction) was then poured off the pellet. The postmitochondrial supernatant (S9 fraction) may be aliquoted and stored at −70° C. in labeled polypropylene bottles.

8. Excessive amounts of lipid were removed from around the mouth of the centrifuge tube (e.g., with a cotton swab) and the crude mitochondrial pellet was resuspended with wash buffer.

9. The centrifuge tubes were filled approximately half-full with wash buffer, and gently vortexed to detach the mitochondrial pellet.

10. The pellet and wash buffer were transferred to a Potter-Elvehj em-type mortar and homogenized with 3-8 passes of a loose-fitting TEFLON® pestle. This step can be repeated several times if necessary, but only after the homogenization tubes have been allowed to cool on ice for at least one minute.

11. The mitochondria was re-pelleted by centrifugation at 7,500-8,000 gmax for 15±1 minutes at 0-8° C., and the supernatant fraction was decanted and discarded.

12. Steps 8 through 11 were then repeated.

13. Excessive lipid was again removed from the wall of the centrifuge tube (e.g., with a cotton swab), and the supernatant fraction was discarded.

14. A small volume of 250 mM sucrose was added to each tube (e.g., for human liver, add 0.5 mL of 250 mM sucrose per gram of wet liver weight). The yield of mitochondria from a liver that is exceptionally fatty or has a large amount of connective tissue may be lower than that from a normal liver. For such livers, less sucrose was added (e.g., 0.15 mL/gram of human liver) so that the concentration of mitochondrial protein stays above 10-20 mg/mL.

15. The mitochondrial pellet was detached from the centrifuge tube by vortex mixing and/or mechanical means. The detached pellet was then transferred to a Potter-Elvehjem-type mortar (typically ~20 mL capacity) on ice and resuspended by homogenization with 3-8 passes of a loose fitting TEFLON® pestle. This step was repeated several times as necessary, but only after the homogenization tubes had been allowed to cool on ice for at least one minute. Additional amount of 250 mM sucrose can be added to extremely viscous suspensions, as long as the protein concentration is kept above 10-20 mg/mL. Intermittent vortex mixing can also be used during homogenization. The estimated final volume of the resuspended mitochondria was then recorded.

16. The mitochondrial fraction was mixed well and then stored bulk in aliquots at −70° C. or below in labeled polypropylene bottles.

Optional: A small amount (typically 10-200 μL) of the resuspended and thoroughly mixed mitochondria may be aliquoted into an appropriately sized and labeled polypropylene tube and stored at −70° C. or below. This aliquot can be used for subsequent determination of protein concentration and/or other assays deemed necessary.

Figure 7:
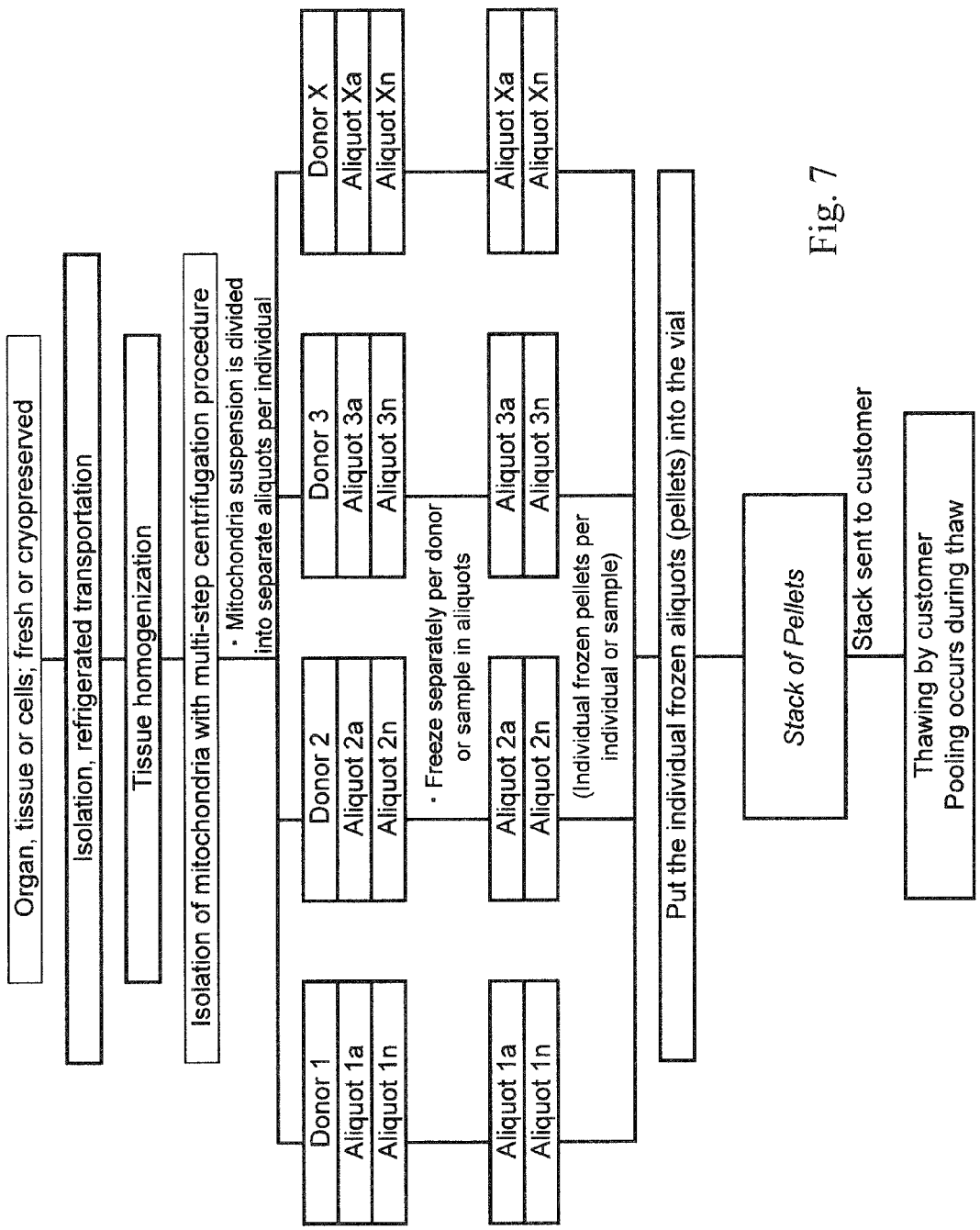
FIG. 7 is a flowchart of a method of isolating and cryopreserving subcellular fractions, such as mitochondria to form a product for creating pooled fractions from different sources via the inventive single-cryopreservation method from Example 6.

17. The suspensions were dispensed into a sterilized pellet holder for cryopreservation, and cryopreserved. The cryopreserved pellets can then be assembled into pre-pooled stacks. This process is outlined in the flowchart in FIG. 7.

Example 7

Comparison of Single and Multi-Cryopreservation on Cryoinjury

In this Example, pooled human hepatocytes products were prepared using the inventive single cryopreserved pellets, along with pooled and non-pooled human hepatocyte products prepared using traditional multi-cryopreservation methods. The products were then thawed and analyzed for enzyme activity. The following enzyme activities were measured in situ: CYP3A4 (testosterone 6-hydroxylation), CYP1A2 (phenacetin O-dealkylation), CYP2B6 (bupropion hydroxylation), FAD-containing monooxygenase (FMO, benzydamine N-oxidation), UDP-glucuronosyltransferase (UGT), and sulfonotransferase (SULT, 7-hydroxycoumarin sulfonation). This Example was used to characterize the effects of single- and multiple-cryopreservation cycles on the CYP- and FMO-mediated oxidation, glucuronidation and sulfation of drugs in individual-donor and pooled-donors hepatocytes.

Hepatocytes were isolated from 4 individuals donors and prepared as non-pooled products using cryopreservation (and thawing) one, two, or threes times. Pooled hepatocytes were also prepared using two protocols. First, using the procedures from Examples 1-3, a stack of 5 single-cryopreserved pellets (five donors) was prepared. Second, multi-cryopreserved pooled products were prepared by obtaining hepatocytes from the same five donors, and cryopreserving according to traditional methods in a vial. The vial contents were then thawed and the thawed products were poured out and pooled together, followed by cryopreserving for a second time to create the cryopreserved pooled product. All cells were stored in the vapor phase of liquid nitrogen and were thawed under the same conditions.

For measurement of enzymatic activity, the cells from each product were rapidly thawed in a water bath at 37° C., and then each transferred to a container containing DMEM with 21.6% PERCOLL®, followed by centrifugation at 80×g for 5 minutes. Following a rinse spin in DMEM at 60×g for 3 minutes, cell viability was measured using Trypan Blue exclusion method, already described. Enzymatic activity was then determined in situ according to the analytical methods in Table 5 below.

TABLE 5

| Enzyme | Substrate (μM) | Metabolite | Incubation time (min) | Cells per incubation | Ionization Mode | Mass Transitions (amu) |
|---|---|---|---|---|---|---|
| CYP1A2 | Phenacetin 100 | Acetaminophen | 30 | 500,000 | ESI− | 150 → 107 |
| CYP2B6 | Bupropion 500 | Hydroxybupropion | 30 | 500,000 | ESI+ | 256 → 238 |
| CYP3A4/5 | Testosterone 250 | 6β-hydroxytestosterone | 30 | 500,000 | ESI− | 303 → 287 |
| Multiple sulfonotransferases | 7-hydroxycoumarin 100 | 7-hydroxycoumarin sulfate | 30 | 500,000 | ESI− | 241 → 161 |
| Multiple UDP-glucuronosyl transferases | 7-hydroxycoumarin 100 | 7-hydroxycoumarin glucuronide | 30 | 500,000 | ESI− | 337 → 161 |
| Multiple UDP-glucuronosyl transferases | 4-methylumbelliferone 1000 | Methylumbelliferone-4-glucuronide | 30 | 500,000 | ESI+ | 353 → 177 |

TABLE 5-continued

| Enzyme | Substrate (µM) | Metabolite | Incubation time (min) | Cells per incubation | Ionization Mode | Mass Transitions (amu) |
|---|---|---|---|---|---|---|
| UGT1A1 | Estradiol 100 | Estradiol-3-glucuronide | 15 | 500,000 | ESI− | 447 → 271 |
| UGT1A4 | Trifluoperazine 25 | Trifluoperazine glucuronide | 30 | 500,000 | ESI+ | 584 → 408 |
| UGT1A6 | Naphthol 500 | Naphthol glucuronide | 7.5 | 125,000 | ESI− | 319 → 143 |
| UGT1A9 | Propofol 50 | Propofol glucuronide | 15 | 125,000 | ESI− | 353 → 177 |
| UGT2B7 | Morphine 1000 | Morphine-3-glucuronide | 15 | 500,000 | ESI+ | 462 → 286 |
| Flavin monooxygenase | Benzydamin 500 | Benzydamine N-oxide | 30 | 500,000 | ESI+ | 326 → 102 |

Figure 8A:
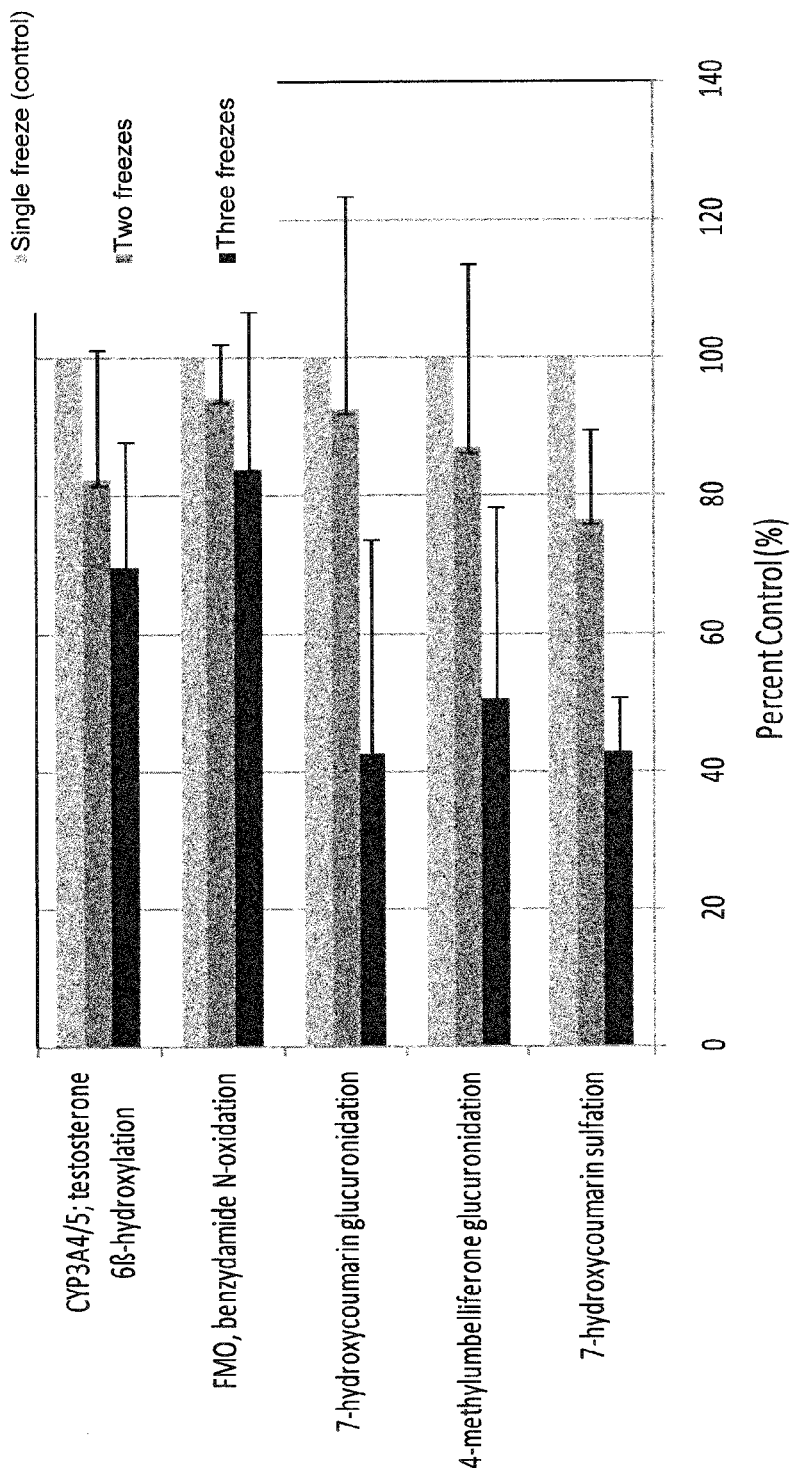
FIGS. 8(A)-8(C) are graphs of the data from the cryoinjury comparison from Example 7.

Hepatocytes from individual donors cryopreserved twice lost, on average, 23% of sulfonotransferase, 18% of CYP3A4, 10% of UDP-glucuronosyltransferase and 6% of FAD-containing monooxygenase activity, as compared to the cells cryopreserved only once. Cells cryopreserved for a third time lost 57% of SULT, 30% of CYP3A4, 54% of UGT and 17% of FMO activity, as compared to the cells cryopreserved once (FIG. 8(A)).

Figure 8B:
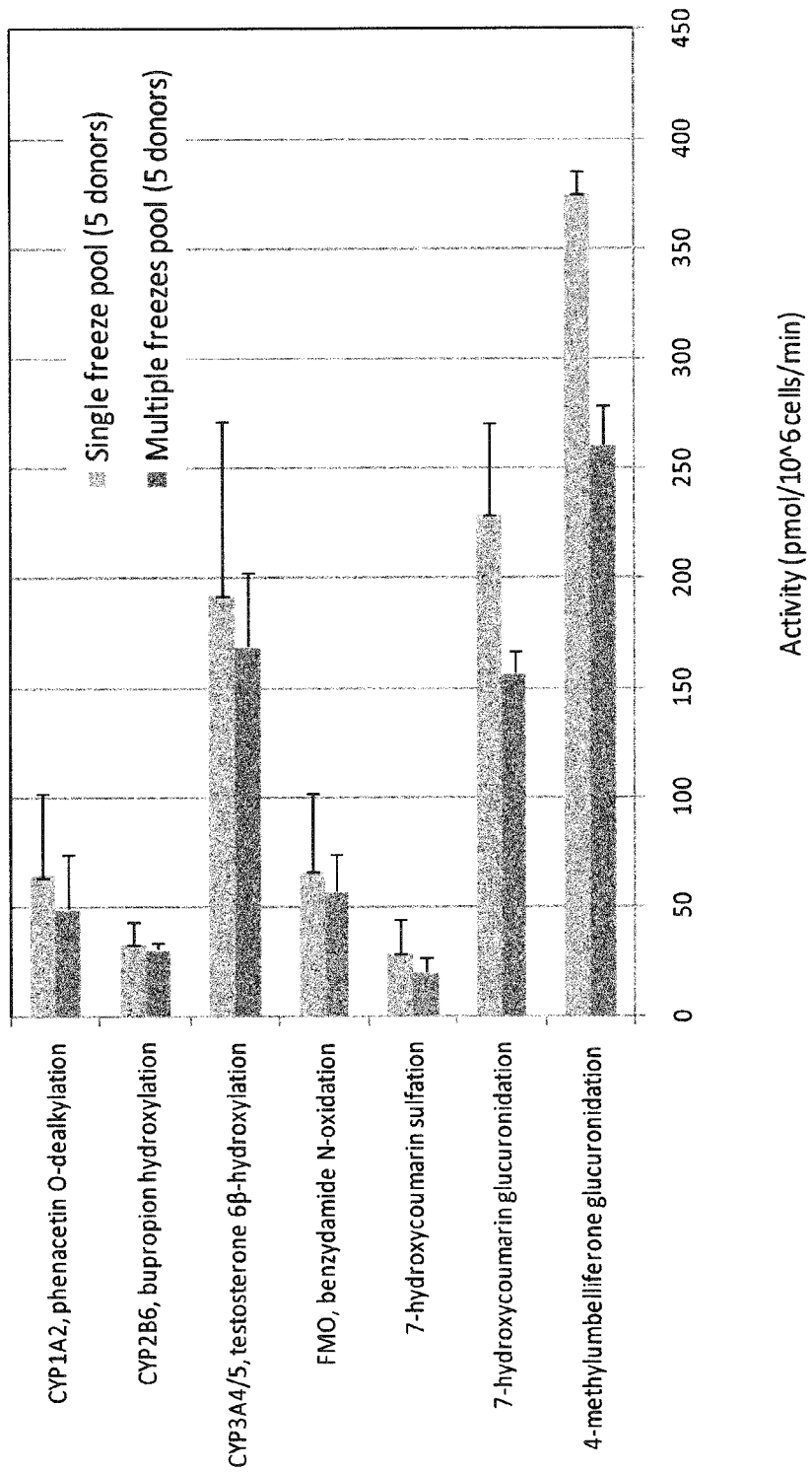

Pooled hepatocytes that were cryopreserved twice lost 33% of SULT, 30% of UGT, 24% of CYP1A2, 14% of FMO, 13% of CYP3A4/5 and 10% of CYP2B6 activity, as compared to the inventive pooled single cryopreserved cells (FIG. 8(B)).

Figure 8C:
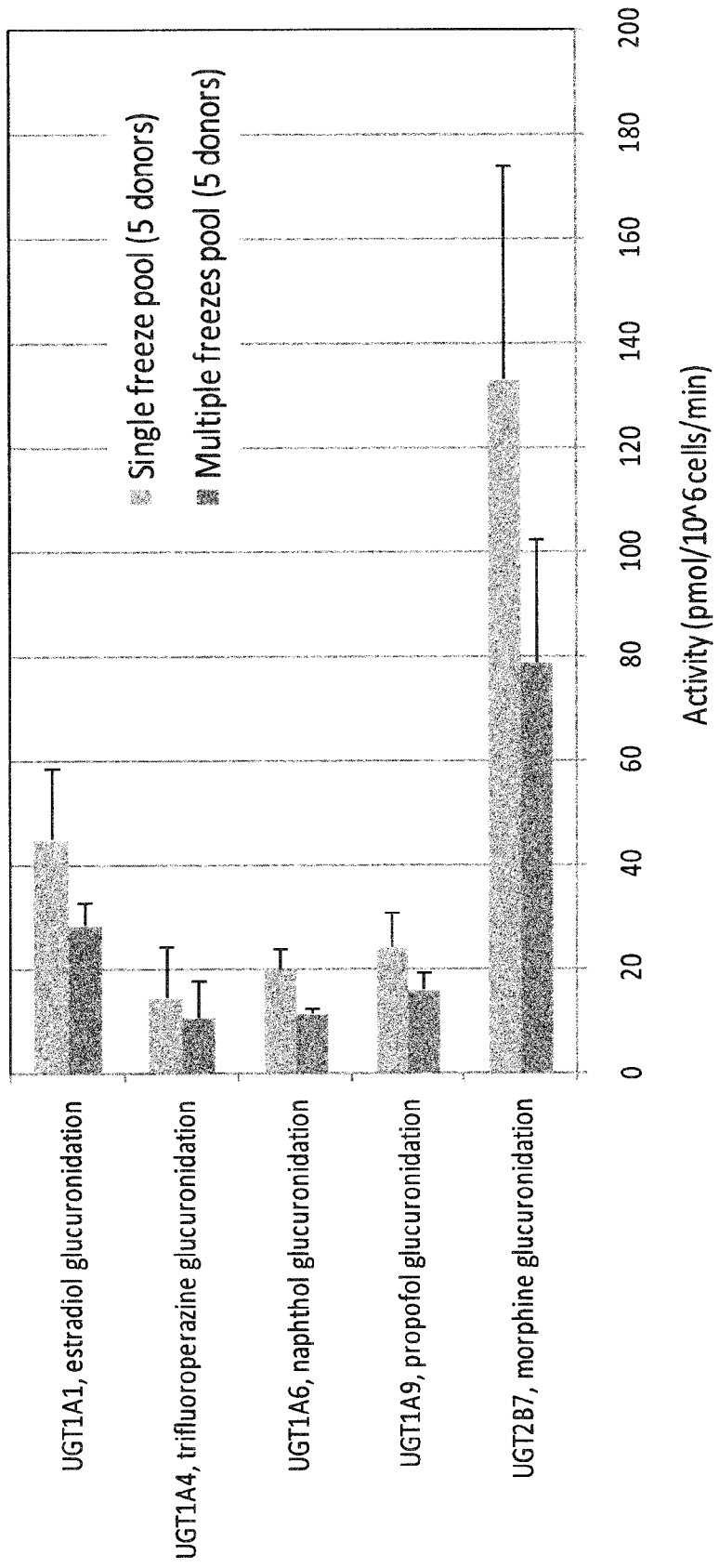

The significant decline in 7-hydroxycoumarine and 4-methylumbelliferone glucuronidation in multi-cryopreserved hepatocytes prompted an isoenzyme-specific analysis of cryoinjury to glucuronidation capacity of the hepatocytes. The UGT1A1, UGT1A4, UGT1A6, UGT1A9 and UGT2B7 lost 37, 26, 43, 34 and 41% of activity in multi-cryopreserved hepatocytes, as compared to the inventive single cryopreserved pooled cells (FIG. 8(C)).

Thus, decline in phase-1 and phase-2 drug metabolism enzymes is one of the manifestations of cryoinjury associated with current methods of preservation of human hepatocytes. In addition, repeated thawing and cryopreservation resulted in a more drastic decline of sulfation and glucuronidation activities than the CYP- or FMO-catalyzed drug oxidation. Pooled hepatocytes cryopreserved once (invention) had phase-1 and phase-2 enzyme activities 26-41% higher than the multi-cryopreserved cells. These data support use of hepatocytes pooled in a cryopreserved state for studies of compounds undergoing significant phase-2 transformation. In summary, multiple cryopreservation cycles have a deleterious effect on the activity of drug-metabolizing enzymes in human hepatocytes. In general, the loss of UGT and SULT activity was more extensive than that of CYP and FMO activity.

What is claimed:

1. A method of forming a pooled preparation of cells, said method comprising:
   providing a pre-pooled stack comprising a combination of cryopreserved cells in a container, said combination of cryopreserved cells comprising:
      a first cryopreserved composition of isolated cells in the form of a first self-sustaining body; and
      a second cryopreserved composition of isolated cells in the form of a second self-sustaining body,
      wherein said first self-sustaining body and said second self-sustaining body are in physical contact with each other in said container, said first cryopreserved composition comprising cells from a different source than said second cryopreserved composition; and
   thawing said stack, wherein said respective first and second cryopreserved compositions, upon thawing, form a single thawed composition comprising said cells from different sources, thereby creating said pooled preparation in situ in said container.

2. The method of claim 1, said first self-sustaining body and said second self-sustaining body remaining discrete bodies in said container until thawing.

3. The method of claim 1, wherein said pre-pooled stack comprises said first self-sustaining body and said second self-sustaining body stacked adjacent one another in said container.

4. The method of claim 1, wherein said first self-sustaining body and said second self-sustaining body can each be handled or moved independently of said container, without being thawed.

5. The method of claim 1, wherein said first self-sustaining body and said second self-sustaining body each have a thickness of from about 2 mm to about 15 mm, and a width of from about 6 mm to about 20 mm.

6. The method of claim 1, wherein said cells are cellular or subcellular fractions selected from the group consisting of mitochondria, cytosol, S9, and microsomes.

7. The method of claim 6, wherein said first self-sustaining body and said second self-sustaining body are each single-cryopreserved compositions of cells.

8. The method of claim 1, each of said first and second cryopreserved composition of isolated cells being formed from a cryopreserved suspension of isolated cells dispersed in a solution comprising a culture medium and a cryoprotectant.

9. The method of claim 1, wherein said container is a vial.

10. The method of claim 1, wherein said cells are hepatocytes.

11. The method of claim 10, wherein said hepatocytes are in a cryopreserved suspension comprising from about 1 million viable hepatocytes/mL to about 20 million viable hepatocytes/mL.

12. The method of claim 10, wherein said hepatocytes are human hepatocytes.

13. The method of claim 1, wherein said thawing comprises placing said container in a water bath at a temperature of from about 35° C. to about 40° C., for about 0.1 to about 4 minutes.

14. The method of claim 1, wherein said cells are hepatocytes, at least about 70% of said hepatocytes in said pooled preparation being viable, based upon the total recovered hepatocytes in the preparation taken as 100%.

15. The method of claim 14, further comprising:
incubating said pooled preparation with a xenobiotic; and
determining a metabolic fate of the xenobiotic, or the effect of the xenobiotic on the hepatocytes in said pooled preparation or on an enzyme or metabolic activity thereof.

16. The method of claim 1, wherein said pre-pooled stack consists of a plurality of said first and second self-sustaining bodies stacked in said container.

17. The method of claim 1, wherein said providing a pre-pooled stack comprises:
providing a first receptacle comprising a plurality of wells configured to contain cells;
adding a quantity of a first composition of cells from a first source to each of said wells;
cryopreserving said first composition to yield discrete cryopreserved self-sustaining bodies formed from said first composition in each of said wells;
removing at least one of said first self-sustaining bodies from said wells to yield said first cryopreserved composition of isolated cells in the form of a first self-sustaining body; and
transferring said first self-sustaining body to said container.

18. The method of claim 17, wherein said container comprises said second cryopreserved composition of isolated cells in the form of a second self-sustaining body, said first self-sustaining body being stacked adjacent said second self-sustaining body in said container.

* * * * *